(12) United States Patent
Tanaka

(10) Patent No.: US 10,201,323 B2
(45) Date of Patent: Feb. 12, 2019

(54) RADIATION IMAGING SYSTEM, CONTROL APPARATUS, CONTROL METHOD, AND STORAGE MEDIUM

(71) Applicant: CANON KABUSHIKI KAISHA, Tokyo (JP)

(72) Inventor: Hikaru Tanaka, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 85 days.

(21) Appl. No.: 14/188,842

(22) Filed: Feb. 25, 2014

(65) Prior Publication Data

US 2014/0258907 A1    Sep. 11, 2014

(30) Foreign Application Priority Data

Mar. 6, 2013  (JP) ................. 2013-044724

(51) Int. Cl.
*G06F 3/0481*   (2013.01)
*A61B 6/00*    (2006.01)
(Continued)

(52) U.S. Cl.
CPC .............. *A61B 6/586* (2013.01); *A61B 6/461* (2013.01); *A61B 6/465* (2013.01); *A61B 6/54* (2013.01); *A61B 6/542* (2013.01); *G06F 19/00* (2013.01); *G16H 40/63* (2018.01); *A61B 6/4233* (2013.01); *A61B 6/56* (2013.01)

(58) Field of Classification Search
CPC ...................................... A61B 6/00
See application file for complete search history.

(56) References Cited

U.S. PATENT DOCUMENTS 6,449,337 B1 *   9/2002   Honda ............... H05G 1/54
                                                       378/117
7,154,994 B2 *  12/2006   Gray .................. A61B 6/4233
                                                       250/370.09
(Continued)

FOREIGN PATENT DOCUMENTS

JP      H10-260486       9/1998
JP      2003-290196     10/2003
(Continued)

OTHER PUBLICATIONS

JButton, Nov. 14, 2012, Stack Overflow.*
(Continued)

*Primary Examiner* — Matthew Ell
*Assistant Examiner* — Mohamed Abou El Seoud
(74) *Attorney, Agent, or Firm* — Venable LLP

(57) ABSTRACT

A radiation imaging system comprising a radiation imaging apparatus and a control apparatus configured to control the radiation imaging apparatus, the control apparatus comprising: a control unit configured to control display of an imaging enable screen that enables the radiation imaging apparatus to perform imaging; an operation detection unit configured to detect operation by an operator; and an inhibition unit configured to inhibit a transition to another screen other than the imaging enable screen when the operation detected by the operation detection unit while the imaging enable screen is displayed by the control unit is operation other than operation for finishing a radiation imaging examination.

17 Claims, 20 Drawing Sheets

| TRANSITION PERMISSION/INHIBITION DETERMINATION TABLE | | | | | |
|---|---|---|---|---|---|
| OPERATION OCCURRENCE CONDITION | EXTERNAL CAUSE | INTERNAL CAUSE | | | |
| | | START/ END EVENT | INTERNAL ERROR EVENT | | |
| RADIATION IMAGING APPARATUS CONNECTED TO CONSOLE | | | Warning (IMAGING CONTINUATION ENABLED) | Error (IMAGING CONTINUATION ENABLED) | Fatal (IMAGING CONTINUATION DISABLED) |
| TYPE A IMAGING APPARATUS | PERMITTED | PERMITTED | PERMITTED | PERMITTED | PERMITTED |
| TYPE B IMAGING APPARATUS | INHIBITED | INHIBITED | INHIBITED | INHIBITED | PERMITTED |
| TYPE C IMAGING APPARATUS (COMMUNICATION IMAGING MODE IS IN USE) | PERMITTED | PERMITTED | PERMITTED | PERMITTED | PERMITTED |
| TYPE C IMAGING APPARATUS (NON-COMMUNICATION IMAGING MODE IS IN USE) | INHIBITED | INHIBITED | INHIBITED | INHIBITED | PERMITTED |
| TYPE A IMAGING APPARATUS + TYPE A IMAGING APPARATUS | PERMITTED | PERMITTED | PERMITTED | PERMITTED | PERMITTED |
| TYPE A IMAGING APPARATUS + TYPE B IMAGING APPARATUS (TYPE A IMAGING APPARATUS IS IN USE) | PERMITTED | PERMITTED | PERMITTED | PERMITTED | PERMITTED |
| TYPE A IMAGING APPARATUS + TYPE B IMAGING APPARATUS (TYPE B IMAGING APPARATUS IS IN USE) | INHIBITED | INHIBITED | INHIBITED | INHIBITED | PERMITTED |
| TYPE B IMAGING APPARATUS + TYPE B IMAGING APPARATUS | INHIBITED | INHIBITED | INHIBITED | INHIBITED | PERMITTED |
| TYPE A IMAGING APPARATUS + TYPE B IMAGING APPARATUS + TYPE C IMAGING APPARATUS (COMMUNICATION IMAGING MODE IS IN USE) | PERMITTED | PERMITTED | PERMITTED | PERMITTED | PERMITTED |
| TYPE A IMAGING APPARATUS + TYPE B IMAGING APPARATUS + TYPE C IMAGING APPARATUS (NON-COMMUNICATION IMAGING MODE IS IN USE) | INHIBITED | INHIBITED | INHIBITED | INHIBITED | PERMITTED |

(51) Int. Cl.
  *G16H 40/63*  (2018.01)
  *G06F 19/00*  (2018.01)

(56)  References Cited

U.S. PATENT DOCUMENTS

2010/0223573 A1*  9/2010  Tanaka .................... A61B 6/00
                                                      715/777
2012/0243664 A1   9/2012  Nishii .......................... 378/98.2

FOREIGN PATENT DOCUMENTS

| JP | 2009-219538 | 10/2009 |
| JP | 2010-273858 | 12/2010 |
| JP | 2012-200286 | 10/2012 |

OTHER PUBLICATIONS

/Java Tutorial How to Use Buttons, Check Boxes, and Radio Buttons, Nov. 7, 2011, Oracle, https://docs.oracle.com/javase/tutorial/uiswing/components/button.html.*

* cited by examiner

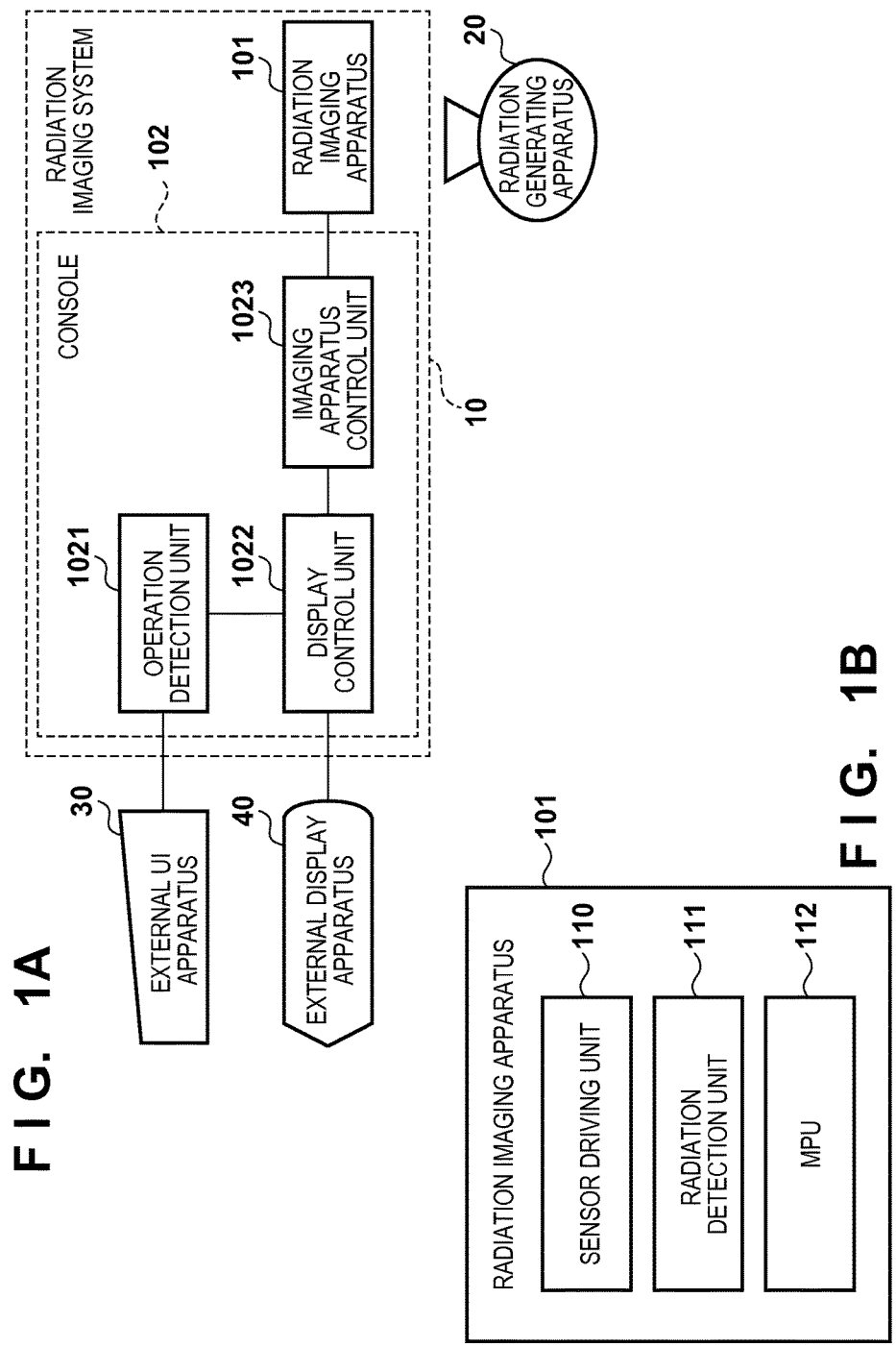

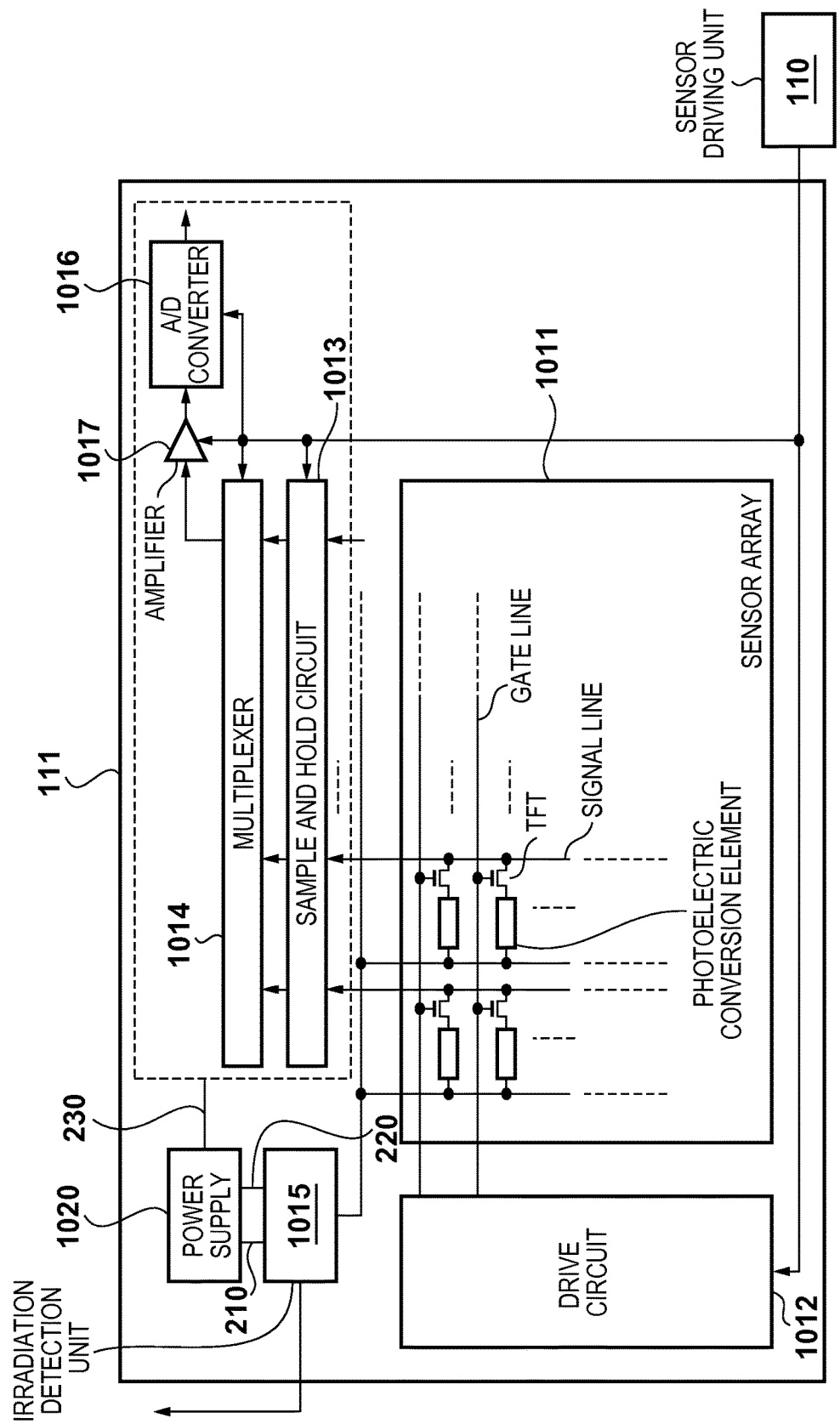

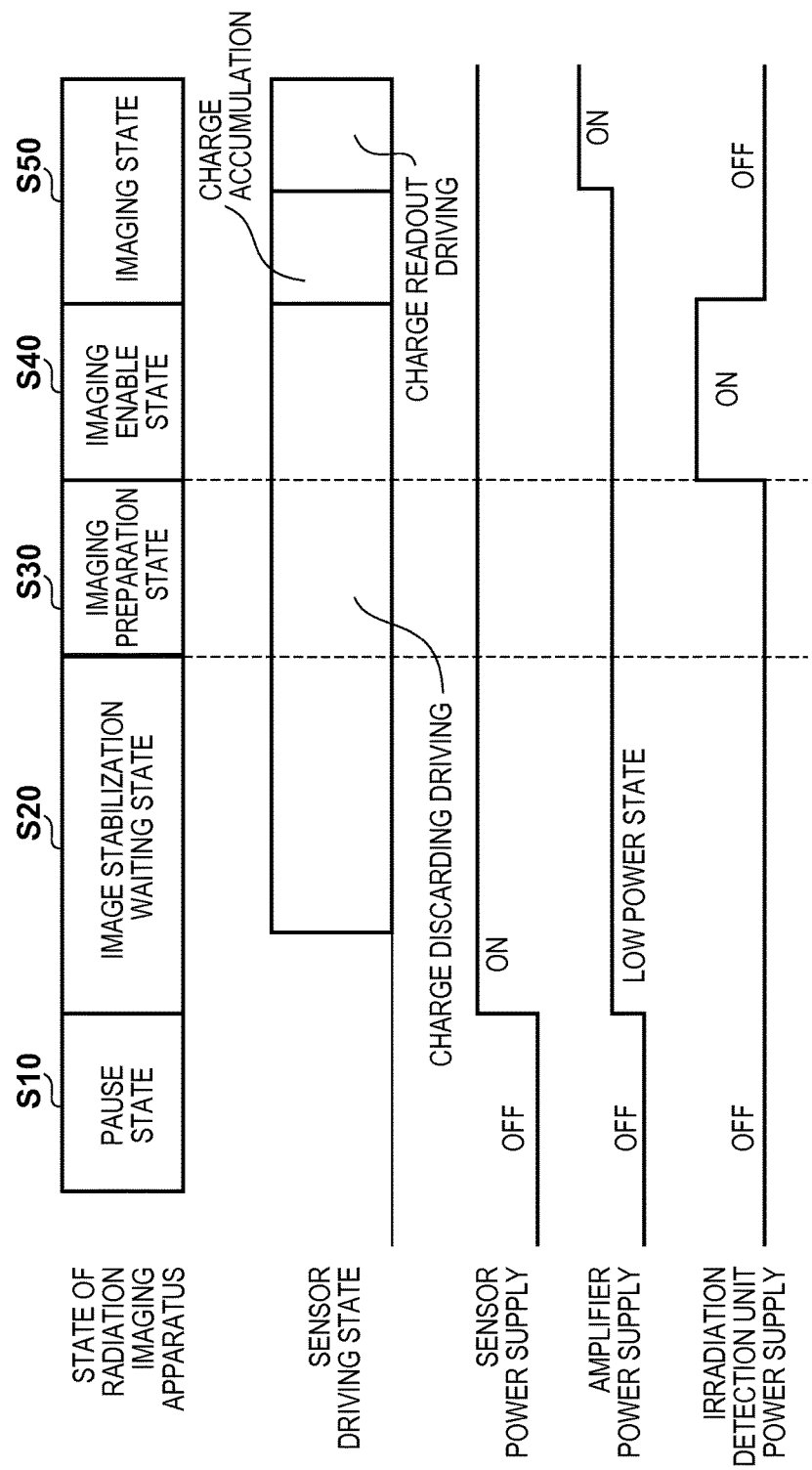

FIG. 3B

| PAST IMAGE | IMAGING SCREEN | SUSPENDED EXAMINATION | SYSTEM |
|---|---|---|---|

PATIENT NAME :
PATIENT ID :
BIRTH DATE :

PATIENT LIST

| PATIENT NAME | PATIENT ID | BIRTH DATE |
|---|---|---|
| MARUKO OTA | 012345 | 1999/01/01 |
| TARO SIMOMARU | 123456 | 1998/02/02 |
| ICHIRO MUSASI | 234567 | 1997/03/03 |
| JIRO NITTA | 345678 | 1996/04/04 |
| SABURO TOKYO | 456789 | 1995/05/05 |
| SHIRO NIHON | 567890 | 1994/06/06 |

EDIT CONDITION ~ 510

~ 403
~ 40

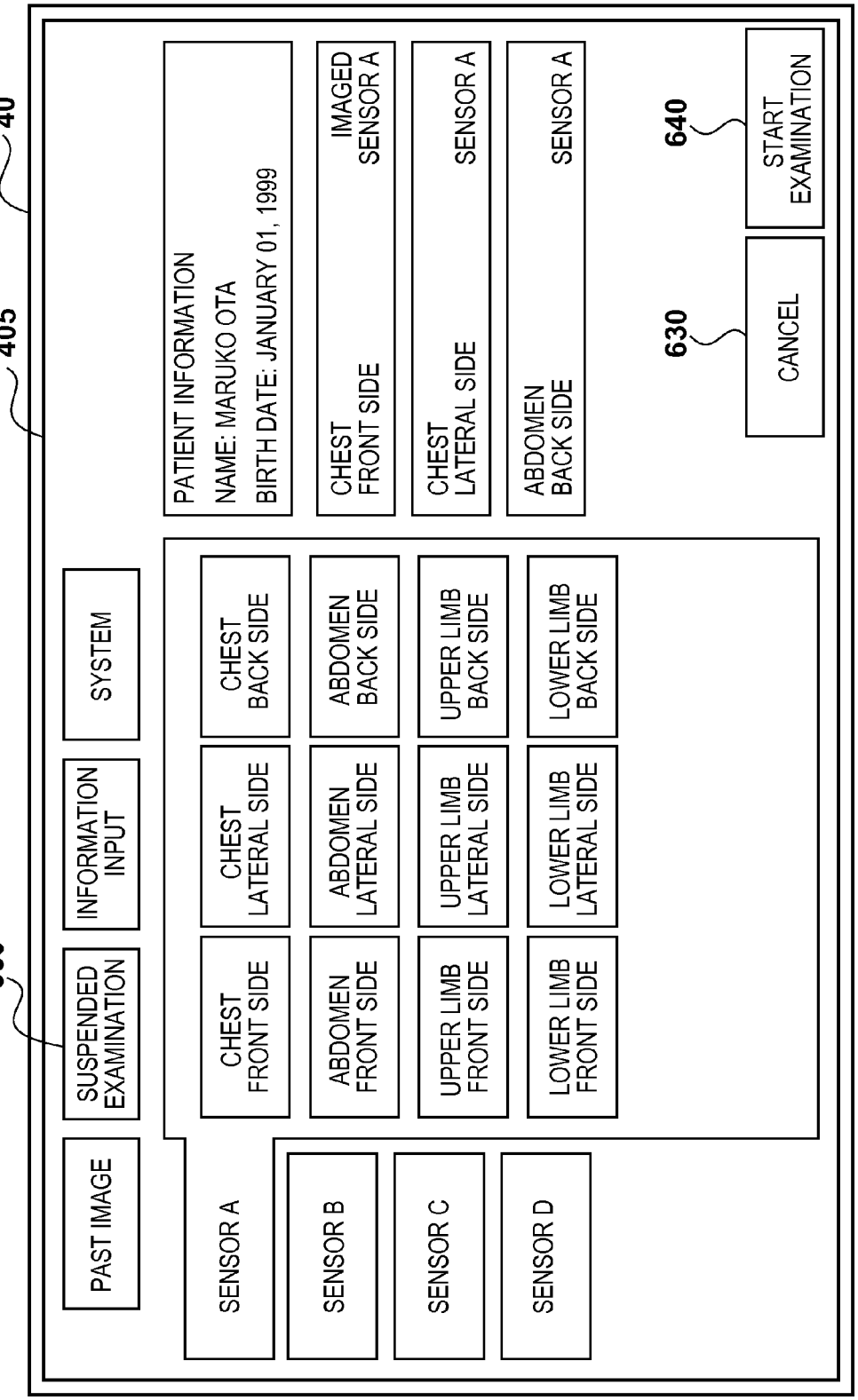

FIG. 5B

PAST IMAGE — 770

| IMAGING SCREEN | INFORMATION INPUT | SYSTEM |

SEARCH LIST
PATIENT ID :
PATIENT NAME :

PATIENT LIST

| PATIENT NAME | PATIENT ID | EXAMINATION DATE |
|---|---|---|
| MARUKO OTA | 012345 | 2013/01/01 |
| TARO SIMOMARU | 123456 | 2013/02/02 |
| ICHIRO MUSASI | 234567 | 2013/03/03 |
| JIRO NITTA | 345678 | 2013/04/04 |
| SABURO TOKYO | 456789 | 2013/05/05 |
| SHIRO NIHON | 567890 | 2013/06/06 |

PATIENT INFORMATION
NAME: MARUKO OTA
BIRTH DATE: JANUARY 01, 1999

| CHEST FRONT SIDE | IMAGED SENSOR A |
| CHEST LATERAL SIDE | SENSOR A |
| ABDOMEN BACK SIDE | SENSOR A |

740 — EDIT CONDITION

730 — START EXAMINATION

| | |
|---|---|
| PAST IMAGE | SYSTEM |

SEARCH LIST
PATIENT ID :
PATIENT NAME :

PATIENT LIST

| PATIENT NAME | PATIENT ID | EXAMINATION DATE |
|---|---|---|
| MARUKO OTA | 012345 | 2013/01/01 |
| TARO SIMOMARU | 123456 | 2013/02/02 |
| ICHIRO MUSASI | 234567 | 2013/03/03 |
| JIRO NITTA | 345678 | 2013/04/04 |
| SABURO TOKYO | 456789 | 2013/05/05 |
| SHIRO NIHON | 567890 | 2013/06/06 |

PATIENT INFORMATION
NAME: MARUKO OTA
BIRTH DATE: JANUARY 01, 1999

CHEST
FRONT SIDE          SENSOR A

CHEST
LATERAL SIDE        SENSOR A

ABDOMEN
BACK SIDE           SENSOR A

START REFERENCE — 810

409    40

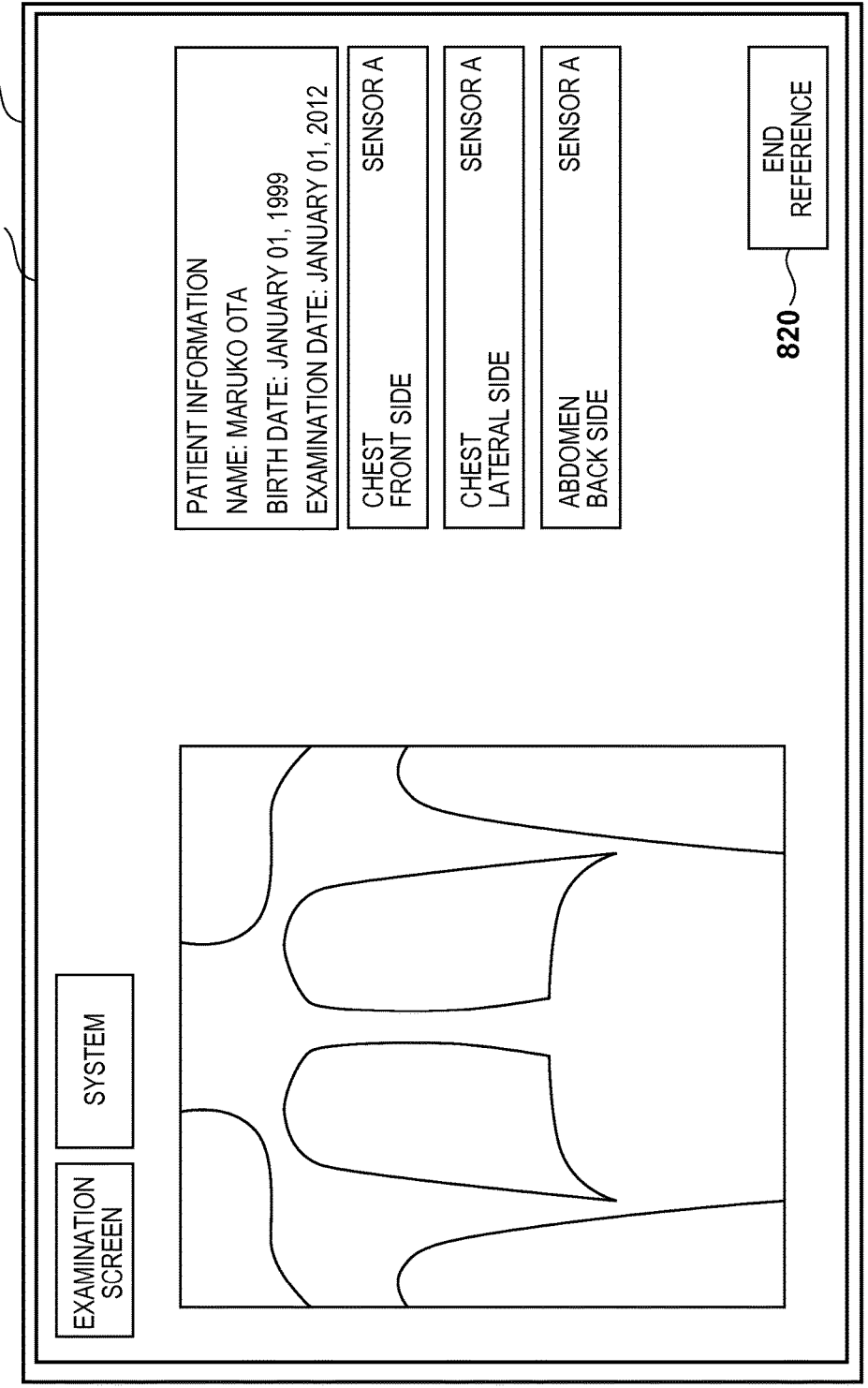

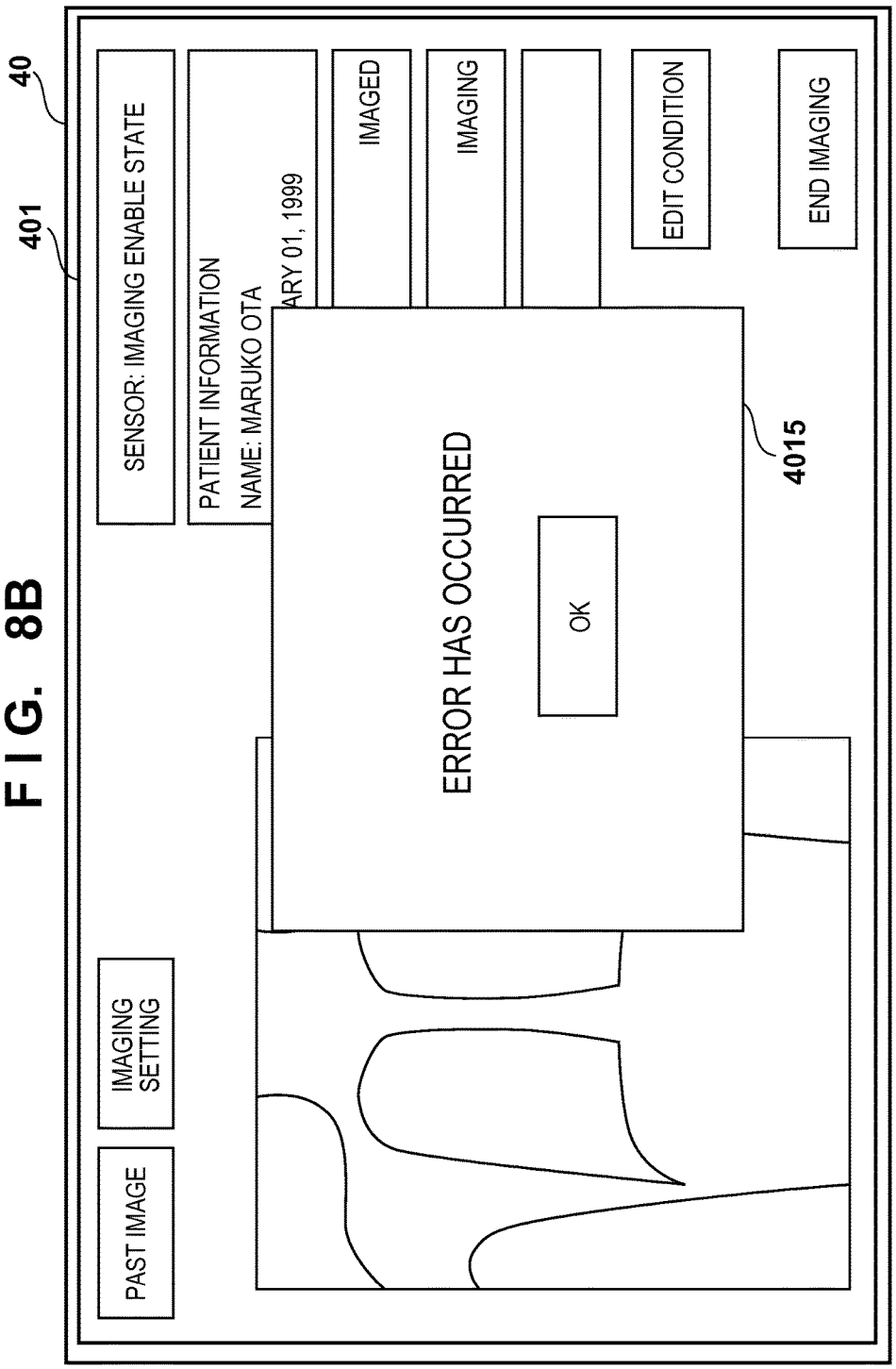

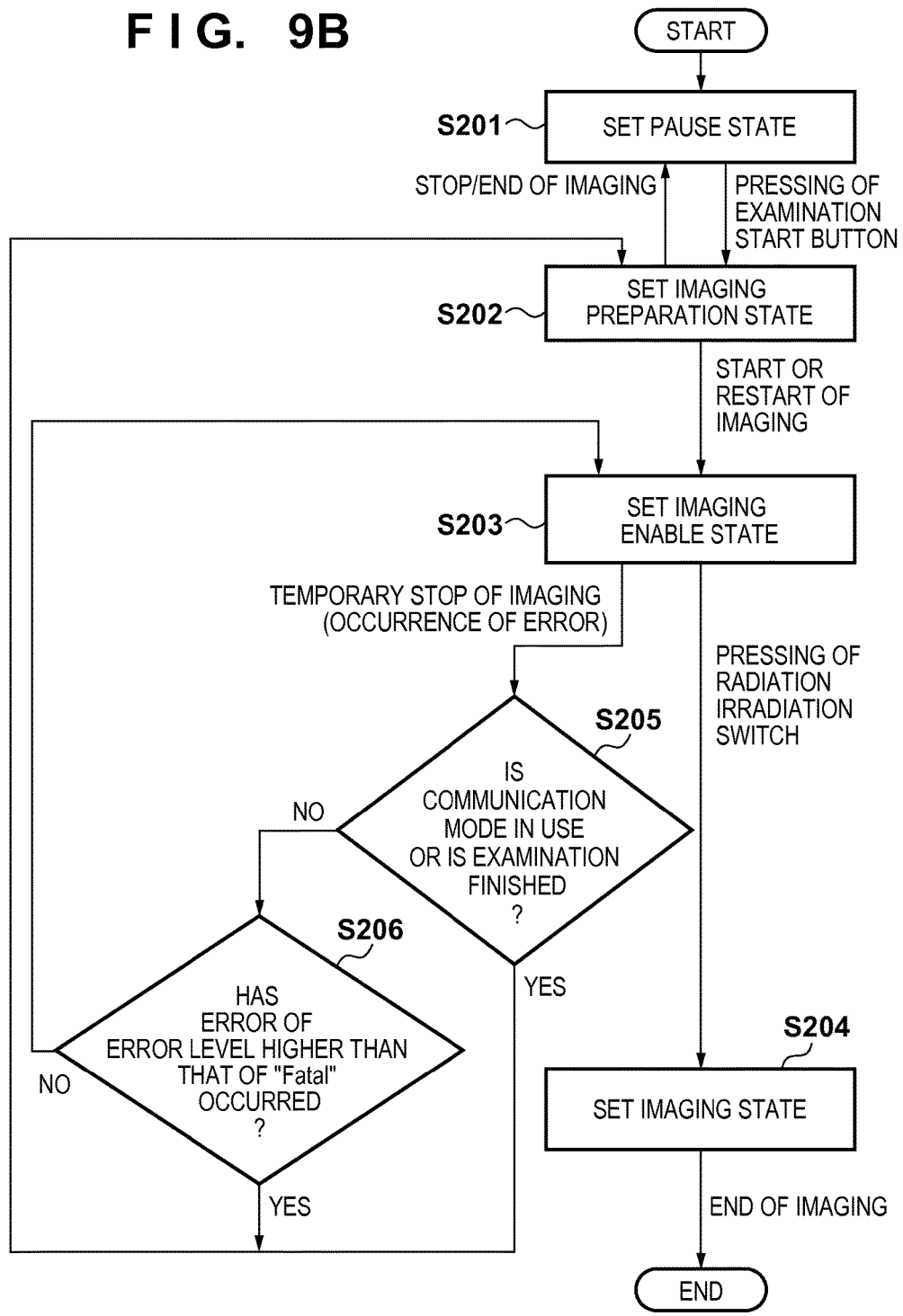

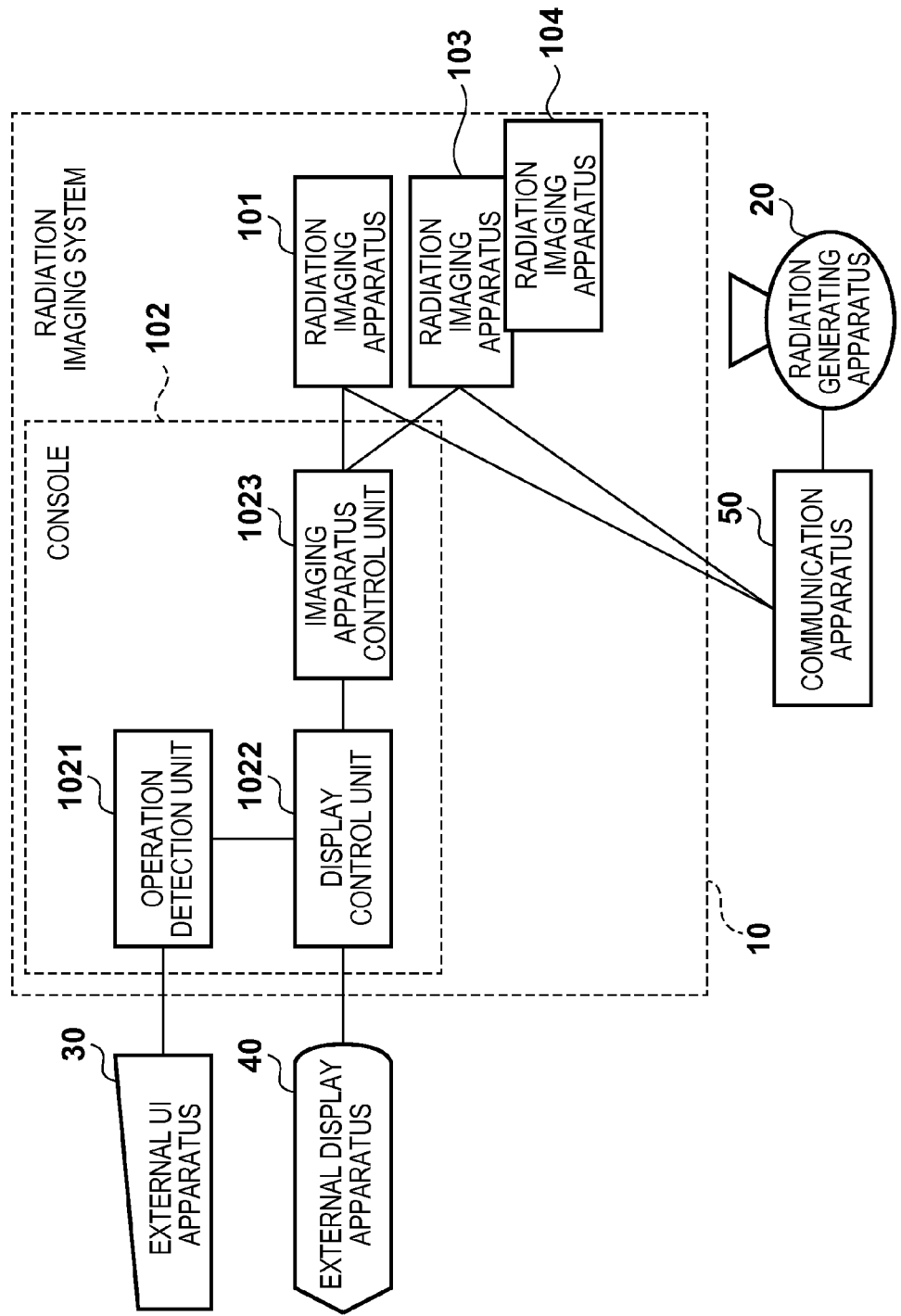

F I G. 11

| TRANSITION PERMISSION/INHIBITION DETERMINATION TABLE | | INTERNAL CAUSE | | | |
|---|---|---|---|---|---|
| | | | INTERNAL ERROR EVENT | | |
| OPERATION OCCURRENCE CONDITION | EXTERNAL CAUSE | START/ END EVENT | Warning (IMAGING CONTINUATION ENABLED) | Error (IMAGING CONTINUATION ENABLED) | Fatal (IMAGING CONTINUATION DISABLED) |
| RADIATION IMAGING APPARATUS CONNECTED TO CONSOLE | | | | | |
| TYPE A IMAGING APPARATUS | PERMITTED | PERMITTED | PERMITTED | PERMITTED | PERMITTED |
| TYPE B IMAGING APPARATUS | INHIBITED | INHIBITED | INHIBITED | INHIBITED | PERMITTED |
| TYPE C IMAGING APPARATUS (COMMUNICATION IMAGING MODE IS IN USE) | PERMITTED | PERMITTED | PERMITTED | PERMITTED | PERMITTED |
| TYPE C IMAGING APPARATUS (NON-COMMUNICATION IMAGING MODE IS IN USE) | INHIBITED | INHIBITED | INHIBITED | INHIBITED | PERMITTED |
| TYPE A IMAGING APPARATUS + TYPE A IMAGING APPARATUS | PERMITTED | PERMITTED | PERMITTED | PERMITTED | PERMITTED |
| TYPE A IMAGING APPARATUS + TYPE B IMAGING APPARATUS (TYPE A IMAGING APPARATUS IS IN USE) | PERMITTED | PERMITTED | PERMITTED | PERMITTED | PERMITTED |
| TYPE A IMAGING APPARATUS + TYPE B IMAGING APPARATUS (TYPE B IMAGING APPARATUS IS IN USE) | INHIBITED | INHIBITED | INHIBITED | INHIBITED | PERMITTED |
| TYPE B IMAGING APPARATUS + TYPE B IMAGING APPARATUS | INHIBITED | INHIBITED | INHIBITED | INHIBITED | PERMITTED |
| TYPE A IMAGING APPARATUS + TYPE B IMAGING APPARATUS + TYPE C IMAGING APPARATUS (COMMUNICATION IMAGING MODE IS IN USE) | PERMITTED | PERMITTED | PERMITTED | PERMITTED | PERMITTED |
| TYPE A IMAGING APPARATUS + TYPE B IMAGING APPARATUS + TYPE C IMAGING APPARATUS (NON-COMMUNICATION IMAGING MODE IS IN USE) | INHIBITED | INHIBITED | INHIBITED | INHIBITED | PERMITTED |

RADIATION IMAGING SYSTEM, CONTROL APPARATUS, CONTROL METHOD, AND STORAGE MEDIUM

BACKGROUND OF THE INVENTION

Field of the Invention

The present invention relates to a radiation imaging system, a control apparatus, a control method, and a storage medium.

Description of the Related Art

Conventionally, there has been commercially available a radiation imaging apparatus which irradiates an object with radiation from a radiation generating apparatus, digitizes a radiation image which is the intensity distribution of radiation transmitted through the object, and generates a clear radiation image by performing image processing for the digitized radiation image, and a radiation imaging system using the radiation imaging apparatus.

In such a radiation imaging system, the radiation generating apparatus irradiates the radiation imaging apparatus with radiation, and the radiation imaging apparatus transfers acquired radiation image data to an image processing apparatus such as a control computer for image processing and storage. The image processing apparatus causes a display apparatus such as a display to display the processed image.

The radiation imaging apparatus forms an image based on an electric signal generated in accordance with radiation. For example, a radiation detection apparatus is configured by stacking a phosphor on each pixel formed from a photoelectric conversion element and the like. The radiation imaging apparatus converts radiation into visible light through the phosphor, holds the visible light in the form of charges, and forms an image from the amount of charge read out.

The radiation imaging apparatus which forms an image from the amount of charge requires a certain time after the energization of a target circuit to enter an imaging enable state for the stabilization of image quality. On the other hand, as a method of saving power by shortening the time to enable imaging, Japanese Patent Laid-Open No. 2010-273858 discloses a method of changing the timeout time after the energization of a circuit for setting an imaging enable state, in accordance with the input state of patient information and an imaging protocol.

In addition, a conventional radiation imaging system is designed to match the timing of radiation generation with the timing of imaging by performing communication between the radiation generating apparatus and the radiation imaging apparatus. Recently, however, as disclosed in Japanese Patent Laid-Open No. 2009-219538, there is known a scheme of performing imaging immediately after the detection of radiation on the radiation imaging apparatus side without performing communication between the radiation generating apparatus and the radiation imaging apparatus. Japanese Patent Laid-Open No. 2009-219538 discloses a method of suppressing a deterioration in image quality by reducing noise and suppressing excess power consumption.

According to the method disclosed in Japanese Patent Laid-Open No. 2010-273858, however, if it takes much time to input patient information and an imaging protocol, the remaining time for actual imaging shortens. For example, timeout may occur during adjustment of the respiratory timing of a patient, resulting in an imaging disable state. This may require a certain waiting time to set an imaging enable state again. In addition, the apparatus disclosed in Japanese Patent Laid-Open No. 2009-219538 may perform radiation irradiation without noticing that it has changed into an imaging disable state to result in failing to capture a desired radiation image (misshooting).

In consideration of the above problem, the present invention provides a technique of reducing the possibility of misshooting by suppressing the occurrence of a screen transition unexpected by an operator at the time of actual imaging while achieving power saving.

SUMMARY OF THE INVENTION

According to one aspect of the present invention, there is provided a radiation imaging system comprising a radiation imaging apparatus and a control apparatus configured to control the radiation imaging apparatus, the control apparatus comprising: a control unit configured to control display of an imaging enable screen that enables the radiation imaging apparatus to perform imaging; an operation detection unit configured to detect operation by an operator; and an inhibition unit configured to inhibit a transition to another screen other than the imaging enable screen when the operation detected by the operation detection unit while the imaging enable screen is displayed by the control unit is operation other than operation for finishing a radiation imaging examination.

Further features of the present invention will be apparent from the following description of exemplary embodiments with reference to the attached drawings.

BRIEF DESCRIPTION OF THE DRAWINGS

FIG. 1A is a block diagram showing an example of the arrangement of a radiation imaging system according to the first embodiment;

FIG. 1B is a block diagram showing the arrangement of a radiation imaging apparatus according to the first embodiment;

FIG. 2A is a block diagram showing an example of the arrangement of a radiation detection unit according to the first embodiment;

FIG. 2B is a chart showing the relationship between the operation state of the radiation imaging apparatus, the driving state of the sensor array of the radiation detection unit, and the power supply states of the respective units (the sensor, amplifier, and irradiation detection unit) of the radiation detection unit;

FIG. 3B is a view showing an example of a patient information input screen 403;

FIG. 5A is a view showing an example of a condition editing screen 405;

FIG. 5B is a view showing an example of a suspended examination screen 406;

FIG. 6B is a view showing an example of a past image selection screen 409;

FIG. 7A is a view showing an example of a past image reference screen 402;

FIG. 8B is a view showing an example of a warning screen 4015;

FIG. 9B is a flowchart showing a processing procedure according to the second embodiment;

FIG. 10A is a block diagram showing an example of the arrangement of a radiation imaging system according to the third embodiment;

FIG. 11 is a view showing an example of a transition permission/inhibition determination table according to the third embodiment.

DESCRIPTION OF THE EMBODIMENTS

Figure 3A:
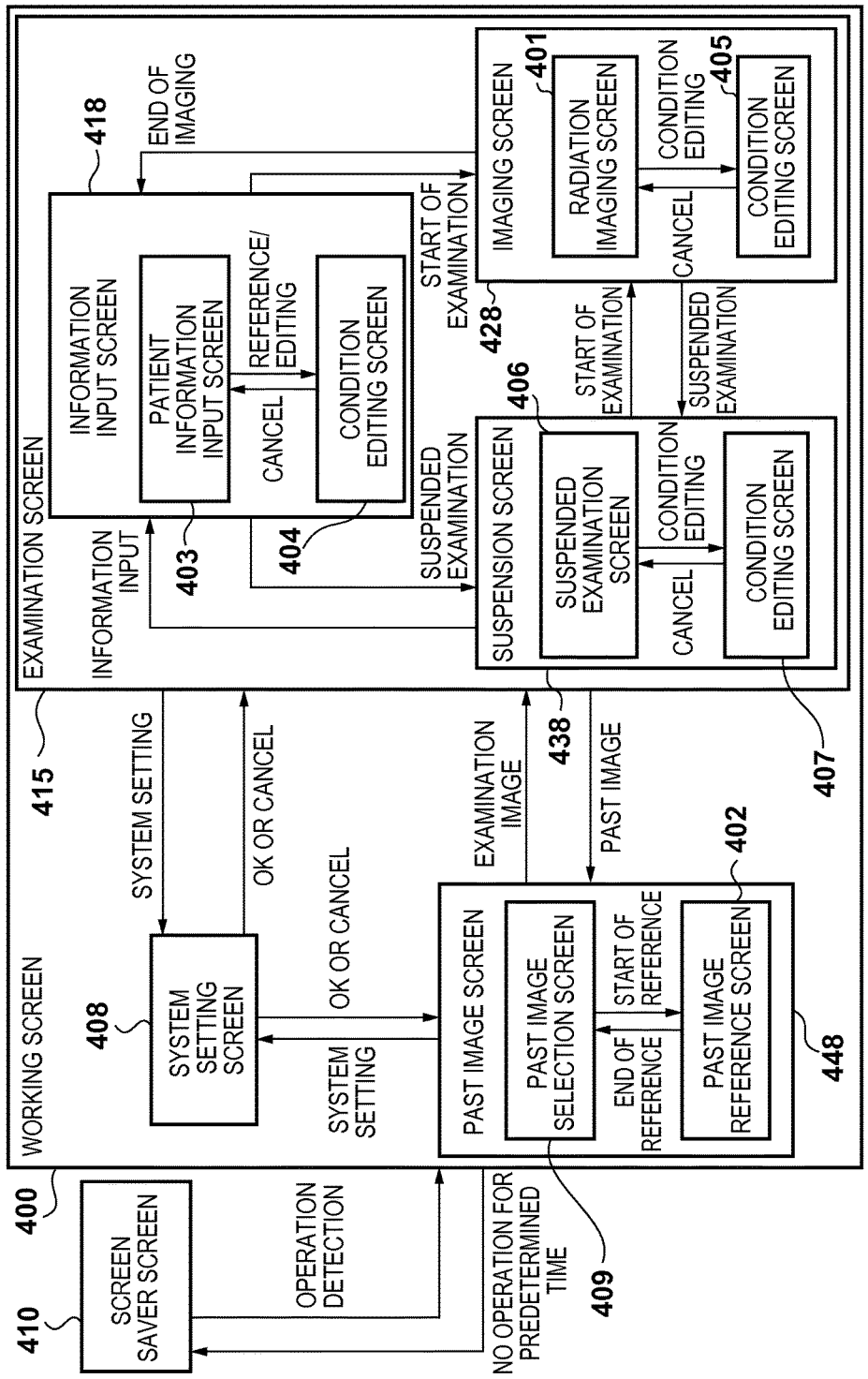
FIG. 3A is a block diagram exemplarily showing the switching of screens (screen transition) to be displayed on an external display apparatus.

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

FIG. 1A is a block diagram showing an example of the arrangement of a radiation imaging system according to the first embodiment. A radiation imaging system 10 includes a radiation imaging apparatus 101 and a console 102 (control apparatus). The radiation imaging apparatus 101 captures a radiation image based on radiation emitted from a radiation generating apparatus 20. The console 102 (control apparatus) controls the operation state of the radiation imaging apparatus 101 to process radiation image data captured by the radiation imaging apparatus 101. The console 102 controls the radiation imaging apparatus 101 based on operation by an external UI apparatus 30 or the instruction generated by internal processing in the console 102. The console 102 includes an operation detection unit 1021, a display control unit 1022, and an imaging apparatus control unit 1023.

The operation detection unit 1021 detects, as operation contents, an input from the external UI apparatus 30 or the instruction generated by internal processing in the console 102. The display control unit 1022 displays, on an external display apparatus 40, a screen for allowing the operator to perform operation or editing in the operation state (for example, the pause state or imaging preparation state) of the radiation imaging apparatus 101, an operation screen corresponding to the operation contents input from the external UI apparatus 30, a captured radiation image, and the like. The display control unit 1022 performs the switching (transition) of display screens based on the operation content detected by the operation detection unit 1021.

The imaging apparatus control unit 1023 issues an instruction to the radiation imaging apparatus 101 to transition to an operation state based on the display contents controlled by the display control unit 1022. The imaging apparatus control unit 1023 also functions as a communication control unit for transmitting/receiving information to/from the radiation imaging apparatus 101.

FIG. 1B is a block diagram showing an example of the arrangement of the radiation imaging apparatus 101. The radiation imaging apparatus 101 includes a sensor driving unit 110, a radiation detection unit 111, and an MPU 112. The radiation detection unit 111 includes a sensor array which detects the radiation emitted from the radiation generating apparatus 20. For example, the radiation detection unit 111 includes a sensor array having a two-dimensional array of pixels, each constituted by a conversion element which converts radiation into an image signal charge (electric signal) and a switch element such as a TFT which transfers an electric signal to the outside. The sensor driving unit 110 drives the radiation detection unit 111. The MPU 112 functions as a control unit which controls the overall operation of the sensor driving unit 110, radiation detection unit 111, and radiation imaging apparatus 101.

FIG. 2A is a block diagram showing an example of the arrangement of the radiation detection unit 111. A drive circuit 1012 simultaneously addresses all the pixels on the rows on a sensor array 1011, which are arranged two-dimensionally. Thereafter, charges (pixel outputs) in the respective pixels held by a sample and hold circuit 1013 are sequentially read out via a multiplexer 1014 and amplified by an amplifier 1017. An A/D converter 1016 converts the resultant charges into image data of a digital value. Every time scanning on each row is complete, the drive circuit 1012 sequentially drives and scans the next respective rows on the sensor array 1011 to finally convert the charges output from all the pixels into digital values. This makes it possible to read out radiation image data. In this case, the apparatus scans the respective pixels on the rows while the voltage applied to each column signal line connected to a corresponding one of the pixels on the rows is fixed to a specific value, and discards the acquired charges to discharge dark charges, thereby discharging (resetting) the dark charges accumulated in the respective pixels. This completes the initialization of the sensor array 1011. The sensor driving unit 110 performs control such as driving control and readout operation control of the radiation detection unit 111.

If the image data converted into a digital value by the A/D converter 1016 is radiation image data obtained by radiation irradiation, it is possible to acquire a captured image from which unnecessary dark charge components are removed, by performing offset correction to subtract the offset image data acquired from only the dark charge components in the respective pixels without radiation irradiation from the radiation image data converted into the digital value.

An irradiation detection unit 1015 detects the start of radiation irradiation. A power supply 1020 supplies power for driving the irradiation detection unit 1015 via a wiring 210. In addition, the power supply 1020 supplies power for driving a sensor (the sensor array 1011 and the drive circuit 1012) via a wiring 220. Furthermore, the power supply 1020 supplies power for driving an amplifier (the sample and hold circuit 1013, the multiplexer 1014, the A/D converter 1016, and the amplifier 1017) via a wiring 230.

The imaging apparatus control unit 1023 controls the timings of supplying power from the power supply 1020 to the irradiation detection unit 1015, the sensor, and the amplifier and the timings of stopping the supply of power. The imaging apparatus control unit 1023 can switch (ON/OFF) the operation states of the irradiation detection unit 1015, sensor, and amplifier by controlling the timings of supplying power.

The operation states of the radiation imaging apparatus 101 include four states, that is, the pause state, the imaging preparation state, the imaging enable state, and the imaging state. The imaging apparatus control unit 1023 controls the operation state of the radiation imaging apparatus 101 by switching energization (power supply) with respect to the sensor driving unit 110 and the radiation detection unit 111.

In the pause state, the imaging apparatus control unit 1023 controls the operation state of the radiation imaging apparatus 101 so as to energize the MPU 112 and stop the energization of the sensor driving unit 110 and radiation detection unit 111. In this pause state, the radiation imaging apparatus 101 cannot perform imaging (imaging disable state). In the pause state, the charges accumulated in the sensor array 1011 of the radiation detection unit 111 are reset (initialization processing). Resetting the accumulated charges can suppress a deterioration in image quality due to the influence of noise, and can enable continuous performance of imaging for a predetermined time (imaging enable limit time) by maintaining the imaging ability.

In the imaging preparation state, the imaging apparatus control unit 1023 controls the operation state of the radiation imaging apparatus 101 so as to energize the MPU 112 and the sensor driving unit 110 and not energize the radiation detection unit 111. In the imaging preparation state, the radiation detection unit 111 is not energized and hence cannot detect the radiation emitted from the radiation generating apparatus 20. Therefore, the radiation imaging apparatus 101 cannot perform imaging (imaging disable state). In the imaging preparation state, the console 102 allows the operator to perform setting and the like for the radiation imaging system, for example, display setting for displaying the image (past image) transmitted from the radiation imaging apparatus 101 in the past, annotation setting, and connection setting with an external apparatus.

Although the imaging preparation state can quickly transition to the imaging enable state, a certain transition time (for example, about 10 sec) needs to elapse between the pause state and the imaging preparation state for the stabilization of image quality (waiting state for image stabilization). As the operator performs preparation work in the imaging enable state, it consumes the imaging enable limit time during which imaging can be continuously performed and shortens the remaining time that enables imaging. In addition, while the operator performs operation such as referring to past images in the imaging enable state, the radiation detection unit 111 is energized without any imaging operation. Such operation is therefore undesirable in terms of power saving. It is preferable to perform operation such as referring to past images in the imaging preparation state. The imaging apparatus control unit 1023 can achieve power saving in the radiation imaging apparatus 101 by controlling the operation state in accordance with operation by the operator.

In the imaging enable state, the imaging apparatus control unit 1023 performs control to energize the MPU 112, the sensor driving unit 110, and the radiation detection unit 111 to enable the respective units to operate. The sensor driving unit 110 drives the radiation detection unit 111. The radiation detection unit 111 detects the radiation generated from the radiation generating apparatus 20 and enters the imaging enable state. In the imaging enable state, since the radiation detection unit 111 is energized, the power consumption is higher than that in the imaging preparation state.

In the imaging state, the sensor driving unit 110 drives the radiation detection unit 111 under the overall control of the imaging apparatus control unit 1023 and the MPU 112, thereby accumulating charges in the respective conversion elements of the sensor array 1011 of the radiation detection unit 111. The sensor driving unit 110 reads out charges accumulated in the respective conversion elements of the sensor array 1011 and forms radiation image data.

FIG. 2B is a chart showing the relationship between the operation state of the radiation imaging apparatus 101, the driving state of the sensor array 1011 of the radiation detection unit 111, and the power supply states of the respective units (the sensor, the amplifier, and the irradiation detection unit 1015) of the radiation detection unit 111. Referring to FIG. 2B, "ON" and "OFF" of the sensor power supply respectively indicate the supply of power (ON) and the stop of power supply (OFF) with respect to the sensor (the sensor array 1011 and the drive circuit 1012).

"ON", "low power state", and "OFF" of the amplifier power supply respectively indicate the supply of power (ON), partial supply of power (low power state), and the stop of power supply (OFF) with respect to the amplifier (the sample and hold circuit 1013, the multiplexer 1014, the A/D converter 1016, and the amplifier 1017). In addition, "ON" and "OFF" of the irradiation detection unit power supply respectively indicate the supply of power (ON) and the stop of power supply (OFF) with respect to the irradiation detection unit 1015.

While the radiation imaging apparatus 101 is in the pause state (S10), the sensor power supply, the amplifier power supply, and the irradiation detection unit power supply are OFF. In the image stabilization waiting state (S20) in the period of transitioning the state of the radiation imaging apparatus 101 from the pause state (S10) to the imaging preparation state (S30), the sensor power supply is ON, the amplifier power supply is in the low power state in which it supplies power to some constituent elements of the amplifier, and the irradiation detection unit power supply is OFF. In the image stabilization waiting state (S20), upon turning on the sensor power supply, the sensor driving unit 110 performs driving to discard charges for the initialization of the sensor array 1011.

In the imaging preparation state (S30), the sensor power supply is ON, the amplifier power supply is in the low power state in which it supplies power to some constituent elements of the amplifier, and the irradiation detection unit power supply is OFF. In the imaging preparation state (S30), the sensor driving unit 110 also performs driving to discard charges for the initialization of the sensor array 1011.

In the imaging enable state (S40), the sensor power supply is ON, the amplifier power supply is in the low power state in which it supplies power to some constituent elements of the amplifier, and the irradiation detection unit power is ON. Turning on the irradiation detection unit power supply enables the irradiation detection unit 1015 to detect the start of radiation irradiation. In the imaging enable state (S40), the sensor driving unit 110 performs driving to discard charges.

In the imaging state (S50), the sensor power supply is ON, and the sensor driving unit 110 controls the driving of the sensor array 1011 to accumulate charges originating from radiation irradiation. In the charge accumulating state, the amplifier power supply is in the low power state. When the sensor driving unit 110 performs driving to read out charges, the amplifier power supply is turned on to enter a higher power supply state than the low power state.

In the imaging state (S50), the irradiation detection unit power supply shifts to the OFF state from the ON state. The imaging apparatus control unit 1023 can achieve power saving in the radiation imaging apparatus 101 by controlling the supply of power to the respective units in accordance with the operation state of the radiation imaging apparatus 101 in this manner.

FIG. 3A is a view exemplarily showing the switching of screens (screen transition) to be displayed on the external display apparatus 40 by the display control unit 1022 of the console 102. The screens in FIG. 3A include a working screen 400 for, for example, inputting information for imaging operation and a screen saver screen 410 which is switched from the working screen when no operation is performed on the radiation imaging apparatus 101 for a predetermined time. When the operation detection unit 1021 detects an operation input while the screen saver screen 410 is displayed, the display control unit 1022 switches the display screen to the working screen 400.

The working screen 400 includes a system setting screen 408, a past image screen 448, and an examination screen 415. The display control unit 1022 switches screen display in accordance with an operation input from each screen.

The past image screen 448 includes a past image selection screen 409 and a past image reference screen 402. The examination screen 415 includes an information input screen 418, an imaging screen 428, and a suspension screen 438. The display control unit 1022 switches screen display in accordance with an operation input from each screen. The information input screen 418 includes a patient information input screen 403 and a condition editing screen 404. The imaging screen 428 includes a radiation imaging screen 401 (imaging enable screen) and a condition editing screen 405. The suspension screen 438 includes a suspended examination screen 406 and a condition editing screen 407.

The details of each screen will be described below with reference to the accompanying drawings. FIG. 3B is a view showing an example of the patient information input screen 403. The operator inputs information about a patient to be imaged as an object from this screen. When the operator presses a condition editing button 510 on the patient information input screen 403, the display control unit 1022 switches the display screen to the condition editing screen 404 (FIG. 4A).

Figure 4A:
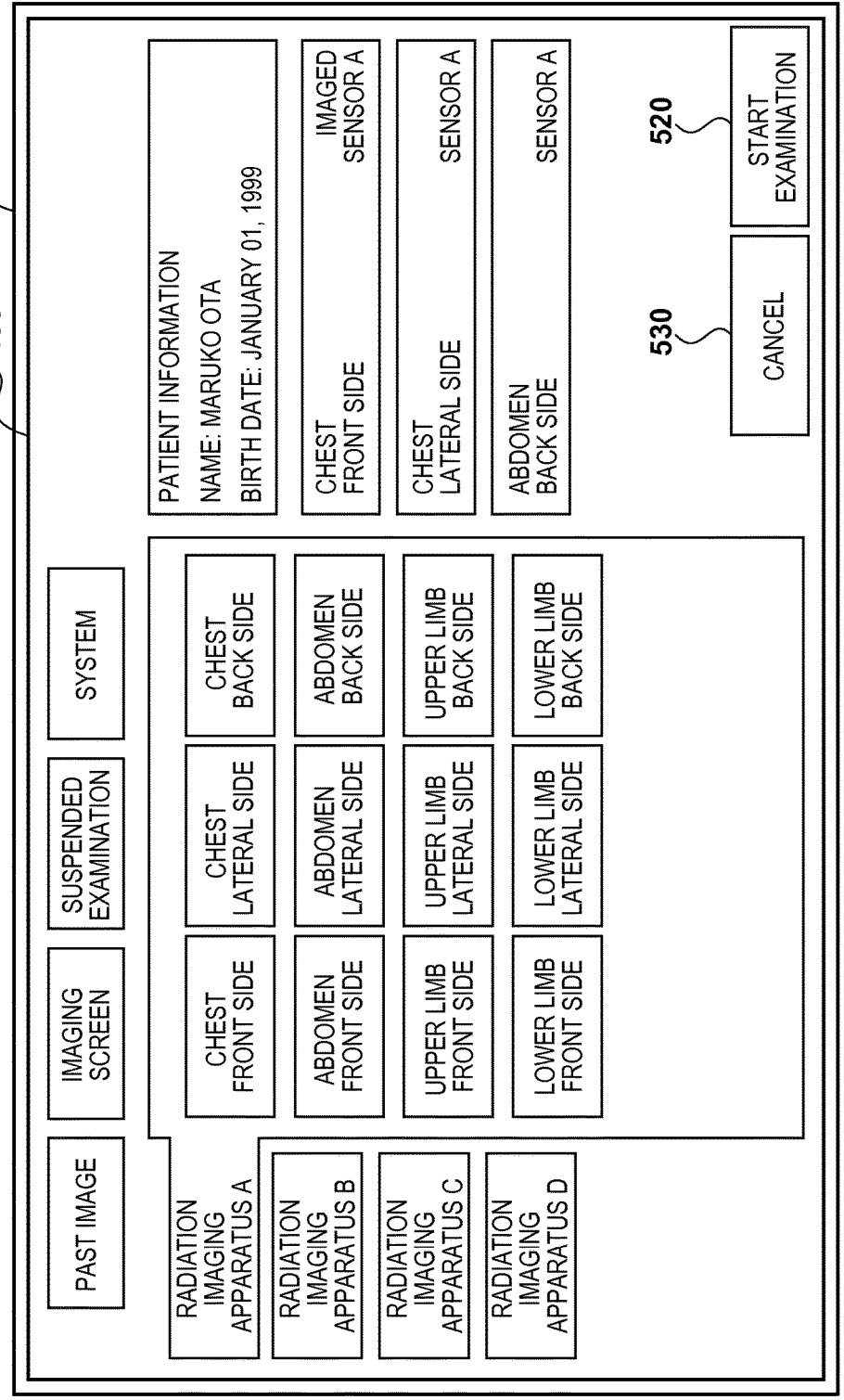
FIG. 4A is a view showing an example of a condition editing screen 404.

FIG. 4A is a view showing an example of the condition editing screen 404. The operator can select a sensor to be used, a region of an object to be imaged, and the like via the condition editing screen 404. When the operator presses a cancel button 530, the display control unit 1022 switches the display screen to return to the patient information input screen 403 (FIG. 3B). When the operator presses the examination start button 520 after inputting information via the patient information input screen 403 and the condition editing screen 404, the display control unit 1022 switches the display screen to the radiation imaging screen 401 (FIG. 4B).

At this time, the operation state of the radiation imaging apparatus 101 transitions from the pause state (S10) to the imaging preparation state (S30) described with reference to FIG. 2B under the control of the imaging apparatus control unit 1023. Note that the imaging apparatus control unit 1023 can also control the operation state so as to automatically transition (automatic transition) from the pause state (S10) to the imaging preparation state (S30) upon completion of information input via the patient information input screen 403 and the condition editing screen 404 regardless of whether the operator presses the examination start button 520.

Figure 4B:
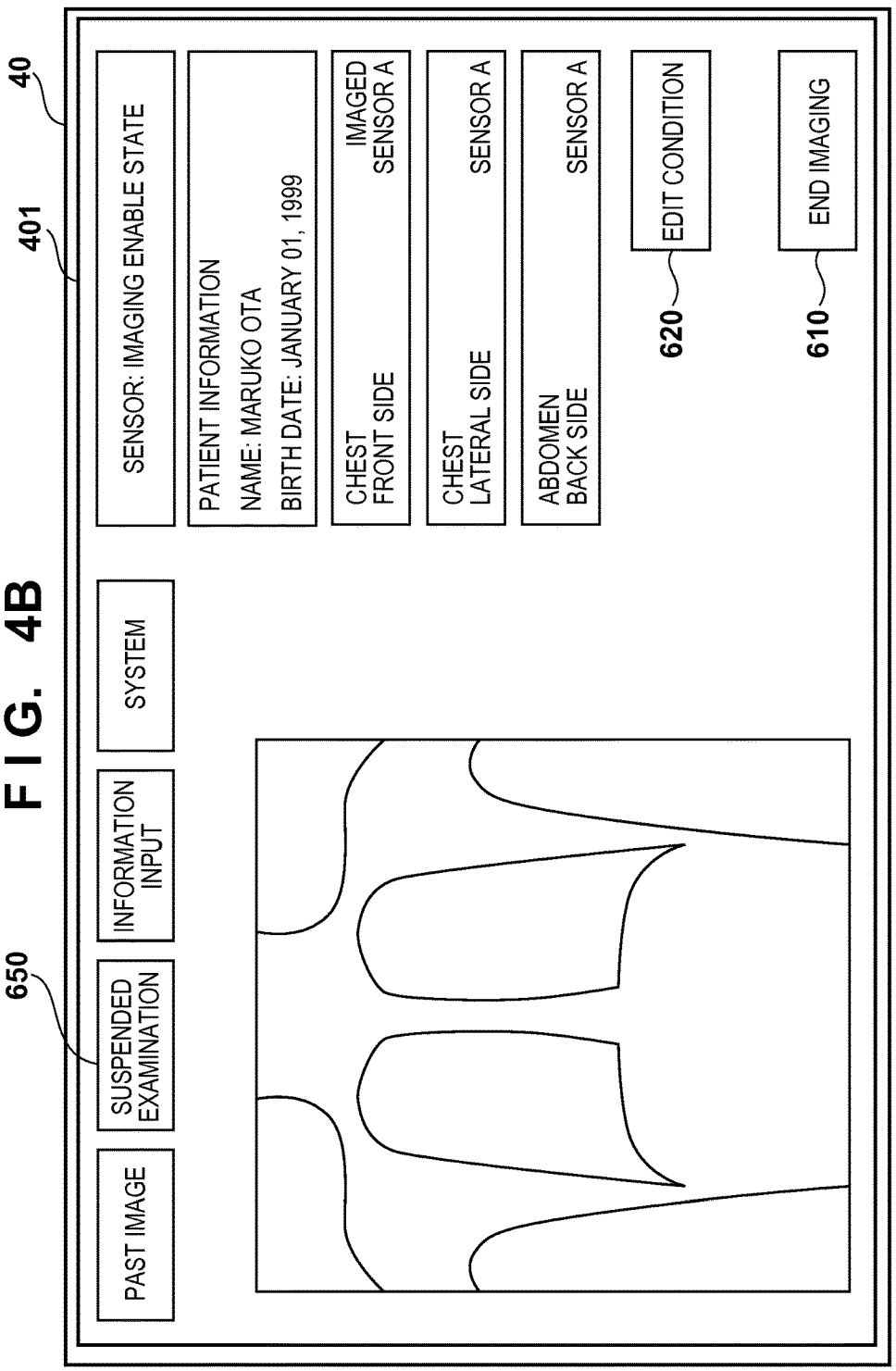
FIG. 4B is a view showing an example of a radiation imaging screen 401.

FIG. 4B is a view showing an example of the radiation imaging screen 401, which is a screen to be displayed when the radiation generating apparatus 20 actually performs radiation irradiation and the radiation imaging apparatus 101 performs radiation imaging. When the operator presses an imaging end button 610, the display control unit 1022 switches the display screen to the patient information input screen 403 (FIG. 3B) for information input for imaging of the next object. When changing imaging conditions, the operator presses a condition editing button 620, the display control unit 1022 switches the display screen to the condition editing screen 405 (FIG. 5A).

FIG. 5A shows an example of the condition editing screen 405 for radiation imaging. The operator can select a sensor to be used, a region of an object to be imaged, and the like via the condition editing screen 405. When the operator presses a cancel button 630, the display control unit 1022 switches the display screen to the radiation imaging screen 401 (FIG. 4B) without reflecting any imaging condition editing result. When the operator presses an examination start button 640, the radiation imaging screen 401 (FIG. 4B) reflecting the imaging condition editing result is displayed.

In addition, when the operator presses the respective suspended examination buttons 650 and 660 on the radiation imaging screen 401 in FIG. 4B and the condition editing screen 405 in FIG. 5A, the display control unit 1022 switches the display screen to the suspended examination screen 406 in FIG. 5B.

FIG. 5B is a view showing an example of the suspended examination screen 406 displaying a list of suspended examinations. When the operator selects a suspended examination of an object (suspended examination) via the suspended examination screen 406 and presses an examination start button 730, the radiation imaging screen 401 (FIG. 4B) corresponding to the selected suspended examination is displayed. On the other hand, when the operator presses a condition editing button 740, the display control unit 1022 switches the display screen to the condition editing screen 407 (FIG. 6A).

Figure 6A:
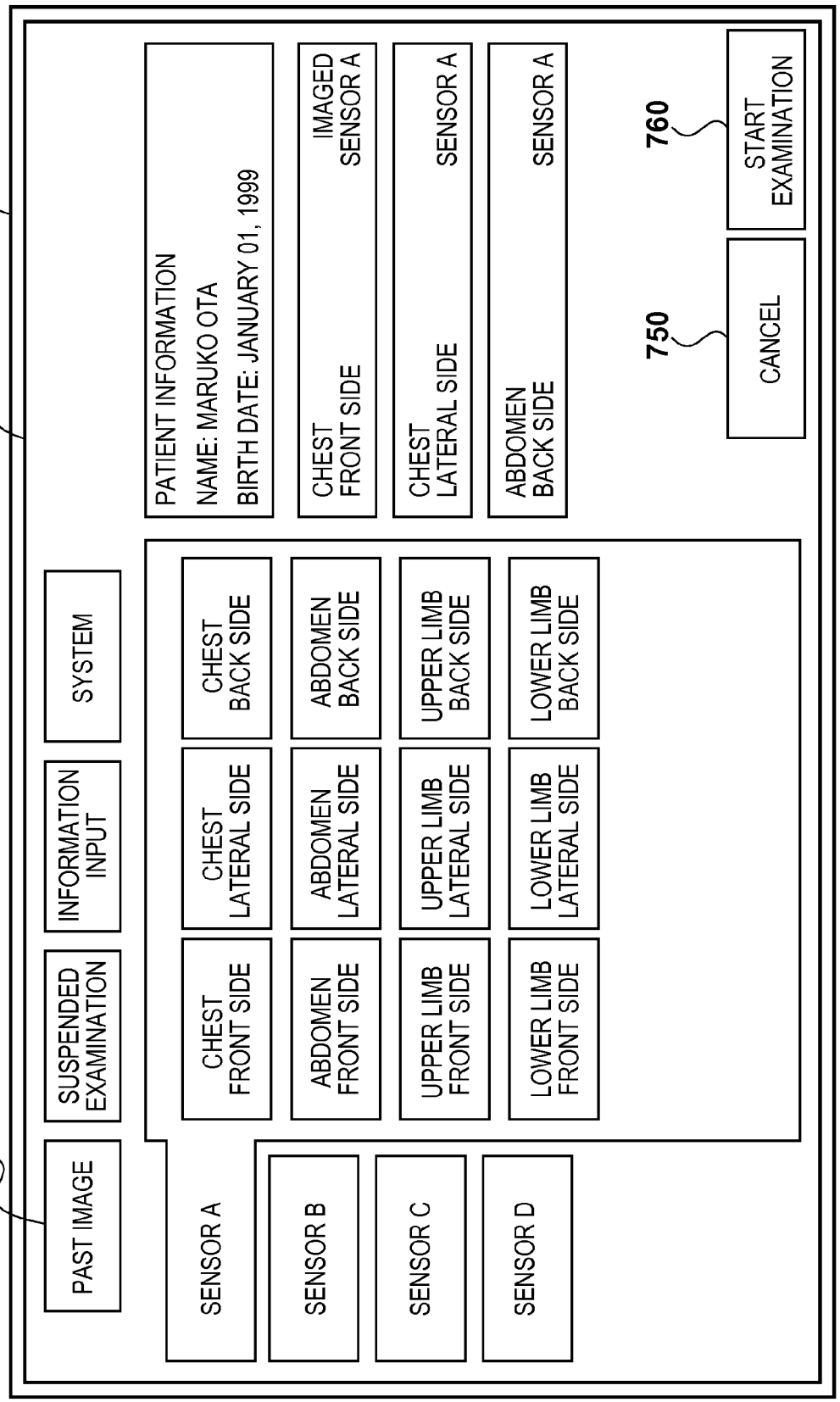
FIG. 6A is a view showing an example of a condition editing screen 407.

FIG. 6A shows an example of the condition editing screen 407 for a suspended examination. The operator can select a sensor to be used for a suspended examination, a region of an object to be imaged, and the like via the condition editing screen 407. When the operator presses a cancel button 750, the display control unit 1022 switches the display screen to the suspended examination screen 406 (FIG. 5B) without reflecting any suspended examination condition editing result. When the operator presses an examination start button 760, the radiation imaging screen 401 (FIG. 4B) reflecting the suspended examination condition editing result is displayed.

When the operator presses past image buttons 770 and 780 on the suspended examination screen 406 (FIG. 5B) and the condition editing screen 407 (FIG. 6A) for a suspended examination, the display control unit 1022 switches the display screen to the past image selection screen 409 (FIG. 6B) for the selection of a patient as a target from a list of patients imaged in the past.

Note that the way of displaying the past image selection screen 409 is not limited to the pressing of the past image buttons 770 and 780 on the suspension screen 438 (the suspended examination screen 406 and the condition editing screen 407). For example, it is also possible to display the above screen by pressing past image buttons on the information input screen 418 (the patient information input screen 403 and the condition editing screen 404) and the imaging screen 428 (the radiation imaging screen 401 and the condition editing screen 405).

FIG. 6B is a view showing an example of the past image selection screen 409 for selecting a target patient from a list of patients imaged in the past. When the operator selects a target patient via the past image selection screen 409 and presses a reference start button 810, the past image reference screen 402 (FIG. 7A) displays an image of the selected patient which was captured in the past.

FIG. 7A is a view showing an example of the past image reference screen 402. When the operator presses a reference end button 820, the display control unit 1022 switches the display screen to the past image selection screen 409 (FIG. 6B).

Figure 7B:
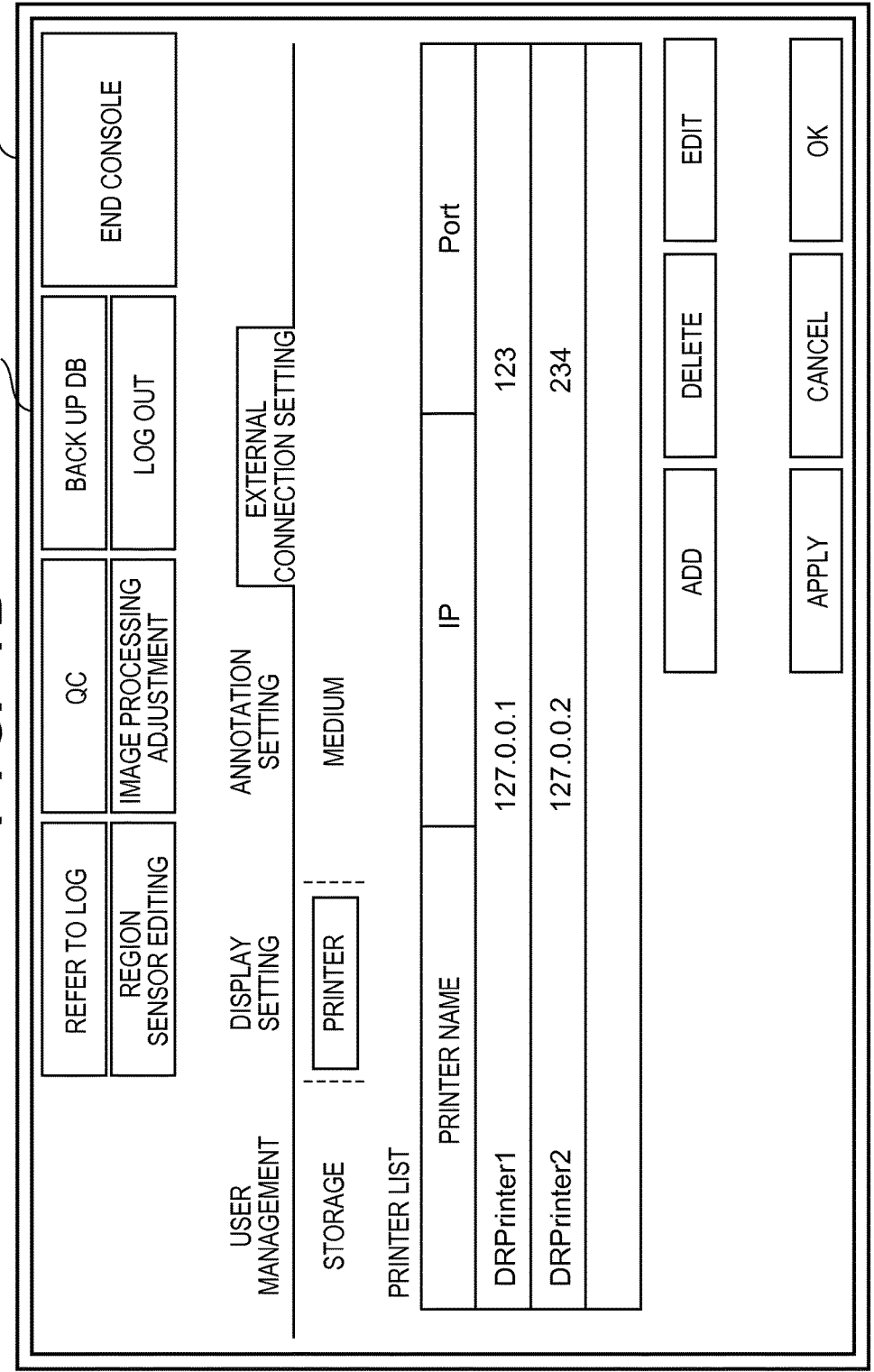
FIG. 7B is a view showing an example of a system setting screen 408.

FIG. 7B is a view showing an example of the system setting screen 408. The operator can perform display setting for displaying the image transmitted from the radiation imaging apparatus 101 and setting for the radiation imaging system such as connection setting with an external apparatus via the system setting screen 408. When the operator presses the system button of each of the examination screen 415 and the past image screen 448, the display control unit 1022 switches the display screen to the system setting screen 408. When the operator presses the application button on the system setting screen 408, the contents of system settings are reflected. When the operator presses the OK button, the display control unit 1022 restores the screen before switching. When the operator presses the cancel button, the display control unit 1022 restores the screen before switching without changing the contents of the system settings.

In addition, the apparatus may be configured to make a transition to either the past image selection screen 409 or the past image reference screen 402 when the operator presses the past image button on each screen described above. In the case shown in FIGS. 6B and 7A, when the operator presses the examination screen button, the display screen returns to the screen before the transition to the past image screen.

In addition, when the operator presses the information input button on each screen, the display screen transitions to either the patient information input screen 403 or the condition editing screen 404. In addition, when the operator presses the imaging screen button on each screen, the display screen transitions to either the radiation imaging screen 401 or the condition editing screen 405.

Furthermore, when the operator presses the suspended examination button on each screen, the display screen transitions to either the suspended examination screen 406 or the condition editing screen 407. When no operation is performed on all the screens for a predetermined time, the display screen transitions to the screen saver screen 410. When the apparatus detects operation, the display screen returns to the previous screen.

Figure 8A:
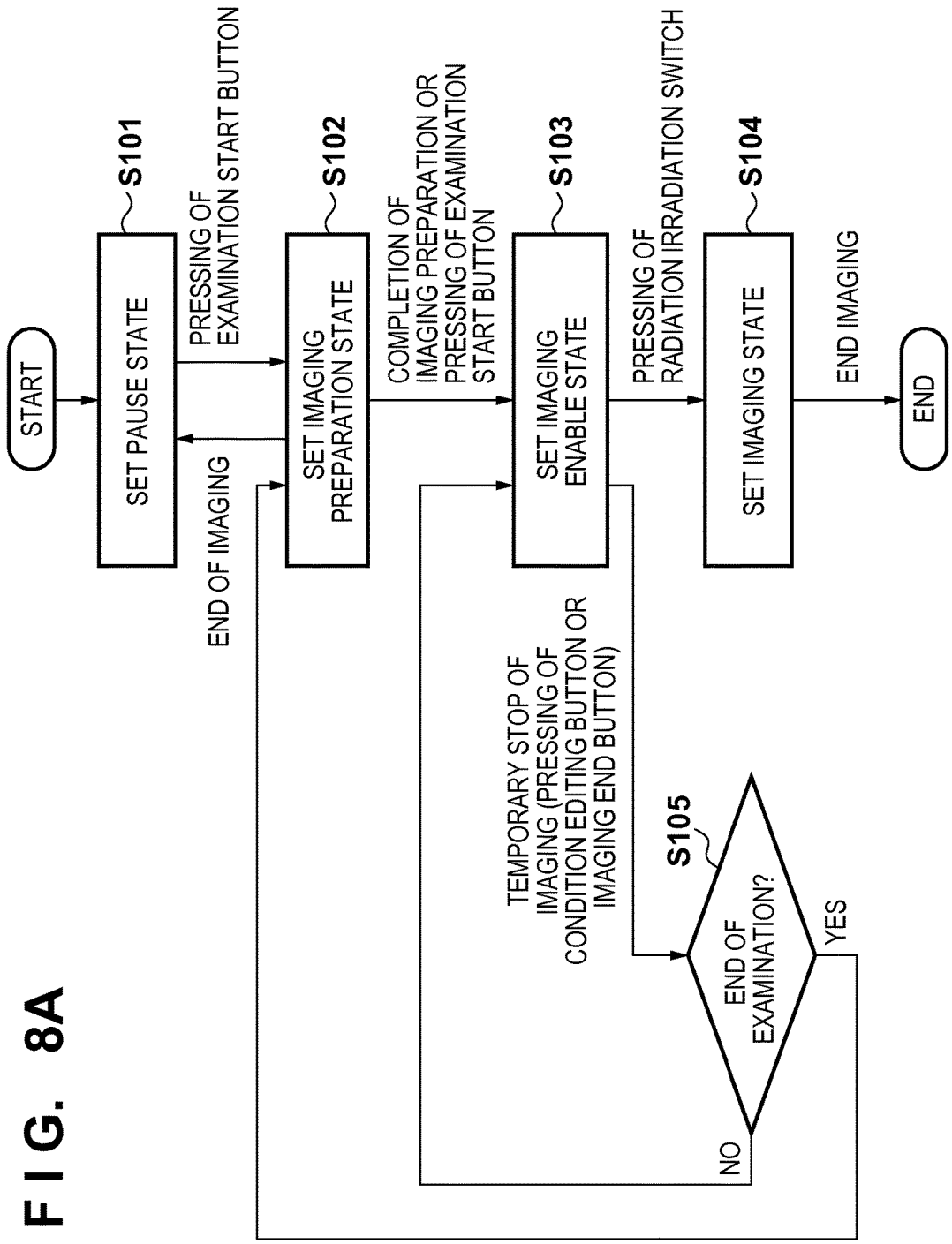
FIG. 8A is a flowchart showing a processing procedure according to the first embodiment.

A processing procedure according to this embodiment will be described below with reference to the flowchart of FIG. 8A. In step S101, the radiation imaging apparatus 101 is in the pause state. When starting imaging preparation, the process shifts to step S102. More specifically, the radiation imaging apparatus 101 displays the condition editing screen (information input screen) 404 on the external display apparatus 40. When the radiation imaging apparatus 101 is in the pause state, the state in step S101 is set. When the operator presses the examination start button 520 on the condition editing screen 404 in step S101, the apparatus makes a screen transition to the radiation imaging screen 401, and the process shifts to step S102 to enter the imaging preparation state.

In step S102, the radiation imaging apparatus 101 is in the imaging preparation state. Upon completion of imaging preparation, the process shifts to step S103 to enter the imaging enable state. When finishing (stopping) the imaging operation, the process shifts to step S101.

In step S103, the radiation imaging apparatus 101 is in the imaging enable state. When, for example, the operator presses the radiation irradiation switch, the process shifts to step S104 to enter the imaging state. On the other hand, when imaging is temporarily stopped, the process shifts to step S105. When, for example, the operator presses the condition editing button 620 on the radiation imaging screen 401 to display the condition editing screen 405 or presses the imaging end button 610, the process shifts to step S105 upon determining that the imaging operation is temporarily stopped.

In step S105, if the operation of temporarily stopping imaging operation is the operation for finishing a radiation imaging examination based on the pressing of the imaging end button 610, the process shifts to step S102. If this operation is operation other than the operation for finishing an examination such as the pressing of the condition editing button 620, the process returns to step S103.

In addition, in step S103, when the operator presses the imaging end button 610, the operation detection unit 1021 detects the operation for finishing imaging operation, and notifies the display control unit 1022 of the operation content. Upon receiving the notification, the display control unit 1022 performs determination in step S105 to finish the examination. In this case, since the detected operation is the operation for finishing the examination, the display control unit 1022 causes the external display apparatus 40 to display a screen after the end of the examination. In addition, the imaging apparatus control unit 1023 issues an instruction to the radiation imaging apparatus 101 to make a transition to the imaging preparation state to enter the imaging preparation state in step S102.

In addition, in step S103, when the operator presses the past image button on the radiation imaging screen 401 to refer to image information captured in the past for an object subjected to radiation imaging, the operation detection unit 1021 also detects the operation for temporarily stopping imaging operation and notifies the display control unit 1022 of the operation content. Upon receiving the notification, the display control unit 1022 performs determination in step S105 to temporarily stop imaging operation. Since the pressing of the past image button is operation other than the operation for finishing an examination, the display control unit 1022 makes no transition to the past image reference screen 402 (FIG. 7A). In addition, the imaging apparatus control unit 1023 does not change the state of the radiation imaging apparatus 101, and hence the imaging enable state indicated by step S103 remains.

Note that although the case in which the operator has pressed the past image button has been described above, the apparatus may be configured in advance to perform screen display processing to inhibit the operator from pressing the past image button when the radiation imaging screen 401 is to be displayed.

In addition, the operation of pressing the system button shown in FIG. 4B and displaying the system setting screen 408 to change system settings for the radiation imaging system 10, including a display control method in the console 102 and communication settings for an external apparatus, is also operation other than the operation for finishing an examination. For this reason, the display control unit 1022 makes no transition to the past image reference screen 402 (FIG. 7A).

The same applies to a case in which an error has occurred in internal processing in the radiation imaging system 10 and the operation detection unit 1021 has detected the error, and to a case in which a screen like an error warning screen 4015 shown in FIG. 8B is superimposed on the radiation imaging screen 401. The same also applies to a case in which when no operation is performed for a predetermined period of time in the radiation imaging system 10, the screen saver screen 410 is displayed.

As described above, in this embodiment, when the radiation imaging apparatus enters the imaging enable state and displays an imaging enable screen, the apparatus inhibits a screen transition to a screen other than the imaging enable screen except for the examination end screen.

This makes it possible to suppress the occurrence of an unexpected screen transition and reduce the possibility of misshooting when the operator actually performs imaging in the scheme of not performing communication between the radiation generating apparatus and the radiation imaging apparatus. In addition, this also produces the effect of being able to ensure a sufficient time for imaging by suppressing operation by the operator.

Second Embodiment

Figure 9A:
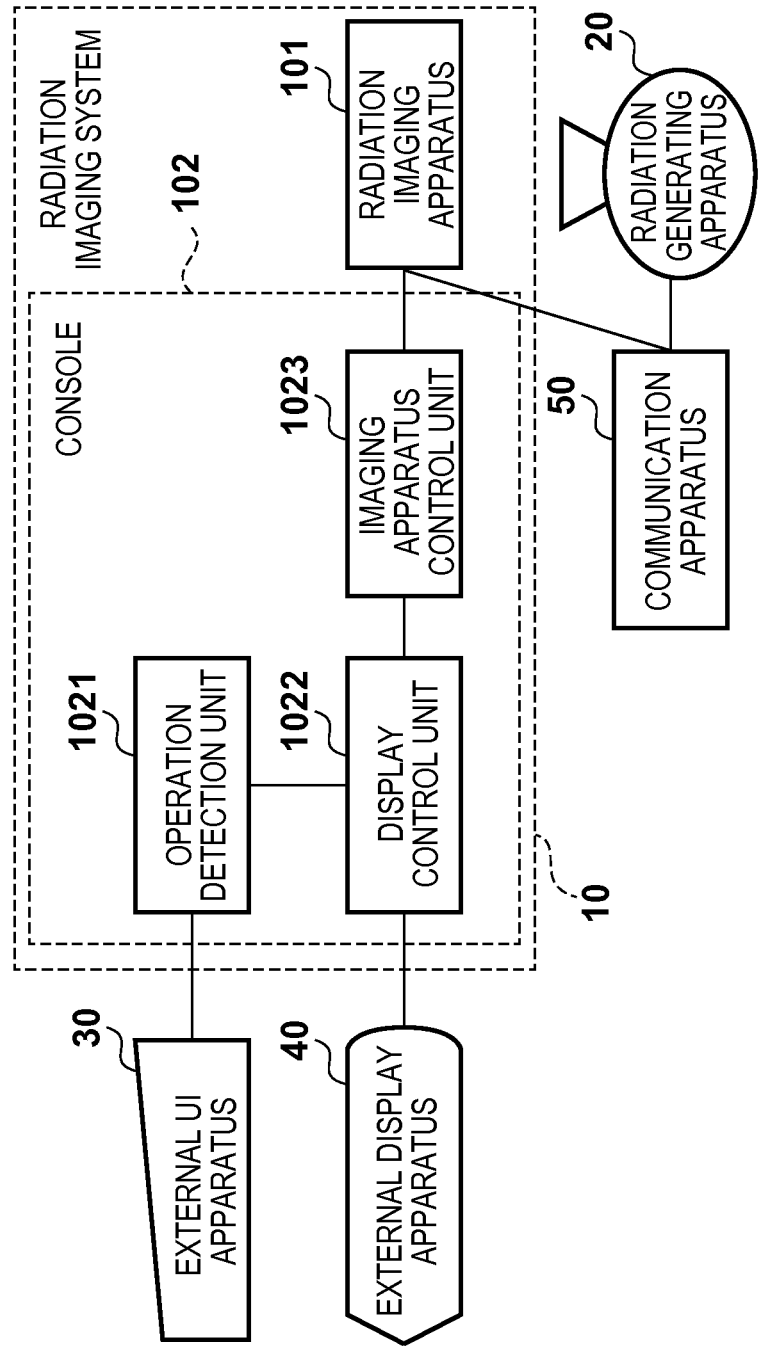
FIG. 9A is a view showing an example of the arrangement of a radiation imaging system according to the second embodiment.

FIG. 9A is a block diagram showing an example of the arrangement of a radiation imaging system 10 according to the second embodiment. A radiation imaging apparatus 101 includes a communication imaging mode of performing radiation imaging while communicating with a radiation generating apparatus 20 via a communication apparatus 50 in addition to a non-communication imaging mode of not performing communication between the radiation generating apparatus and the radiation imaging apparatus. The radiation imaging apparatus 101 can use these modes by switching them. Other constituent elements are the same as those of the first embodiment, and a description of them will be omitted.

A processing procedure according to this embodiment will be described below with reference to the flowchart of FIG. 9B.

In step S201, the radiation imaging apparatus 101 is in the pause state. In step S201, when the operator presses an examination start button 520 on a condition editing screen 404 (FIG. 4A), the display screen transitions to a radiation imaging screen 401 (FIG. 4B), and the process shifts to step S202.

In step S202, the radiation imaging apparatus 101 is in the imaging preparation state, and the process shifts to step S203 when imaging preparation is complete. When stopping/finishing the imaging operation, the process shifts to step S201.

In step S203, the radiation imaging apparatus 101 is in the imaging enable state, and a display control unit 1022 causes an external display apparatus 40 to display the radiation imaging screen 401. In this case, when the radiation generating apparatus 20 starts radiation irradiation in response to the time when the operator presses the radiation irradiation switch, the process shifts to step S204. When temporarily stopping the imaging operation, the process shifts to step S205.

In step S204, the radiation imaging apparatus 101 is in the imaging state. When the imaging operation is complete, the apparatus terminates the processing.

In step S205, when the operator has performed the operation of temporarily stopping the imaging operation in step S203, the radiation imaging apparatus 101 determines whether it is operating in the communication imaging mode or has performed the operation for finishing an examination. If the radiation imaging apparatus 101 determines that it is operating in the communication imaging mode or has performed the operation for finishing an examination, the process shifts to step S202. If the radiation imaging apparatus 101 determines that it is operating in the non-communication imaging mode and has performed operation other than the operation for finishing an examination, the process shifts to step S206.

If the operation of temporarily stopping imaging operation originates from automatic detection of an error by internal processing in the radiation imaging system 10, the apparatus determines an error level in step S206. In this embodiment, an error that disables the continuation of radiation imaging is called a fatal error. If the error level is that of a fatal error, the process shifts to step S202. If the error level is a level other than that of a fatal error, the process shifts to step S203.

Processing corresponding to the type of imaging mode and an error level will be described in detail below. In step S203, when an error that enables continuation of radiation imaging occurs inside the radiation imaging system 10, for example, in a console 102, an operation detection unit 1021 automatically detects the error that has occurred, and notifies the display control unit 1022 of the detection content.

Upon receiving the notification, the display control unit 1022 determines the imaging mode of the radiation imaging apparatus 101 in step S205.

If the radiation imaging apparatus 101 is operating in the communication imaging mode, the display control unit 1022 causes the external display apparatus 40 to display the warning screen 4015 shown in FIG. 8B. In addition, an imaging apparatus control unit 1023 issues an instruction to the radiation imaging apparatus 101 to make a transition to the imaging preparation state in step S203.

If the radiation imaging apparatus 101 is operating in the non-communication imaging mode, the apparatus determines that error detection inside the apparatus is operation other than the operation for finishing an examination. The apparatus therefore determines an error level as in step S206. In this embodiment, upon determining that the detected error is other than a fatal error that enables the continuation of radiation imaging, the display control unit 1022 performs no screen transition. In addition, the imaging apparatus control unit 1023 does not issue an instruction to make a state transition to the radiation imaging apparatus 101. The radiation imaging apparatus 101 remains in the imaging enable state as shown in step S203.

In contrast to this, if the detected error is an error (fatal error) that disables the continuation of radiation imaging, which has occurred in the radiation imaging apparatus 101, the display control unit 1022 causes the external display apparatus 40 to display a warning screen 4015 like that shown in FIG. 8B. In addition, the imaging apparatus control unit 1023 issues an instruction to the radiation imaging apparatus 101 to make a transition to the imaging preparation state in step S202.

As described above, in this embodiment, when the radiation imaging apparatus enters the imaging enable state and displays the imaging enable screen, the apparatus controls the inhibition of a transition to a screen other than the examination end screen in accordance with the error level that has occurred or the imaging mode.

This makes it possible to suppress the occurrence of an unexpected screen transition and reduce the possibility of misshooting when the operator actually performs imaging in a case in which the radiation imaging apparatus operates in the non-communication imaging mode of not performing communication between the radiation generating apparatus and the radiation imaging apparatus. In addition, suppressing operation by the operator produces the effect of being able to ensure a sufficient time for imaging. Furthermore, since it is possible to suppress the occurrence of a screen transition when an error level is not significant, it is possible to further reduce the possibility of misshooting.

Third Embodiment

FIG. 10A is a block diagram showing an example of the arrangement of a radiation imaging system 10 according to the third embodiment.

The differences between the first and second embodiments will be mainly described below. A radiation imaging apparatus 101, a radiation imaging apparatus 103, and a radiation imaging apparatus 104 are radiation imaging apparatuses which generate radiation images by detecting the radiation received from a radiation generating apparatus 20.

Each radiation imaging apparatus has either or both of imaging modes, namely the non-communication imaging mode of starting radiation accumulation driving operation upon automatically detecting received radiation without performing communication with the radiation generating apparatus 20, and the communication imaging mode of performing radiation imaging while communicating with the radiation generating apparatus 20 via a communication apparatus 50. A radiation imaging apparatus having both the imaging modes can perform radiation imaging by switching the imaging modes.

Figure 10B:
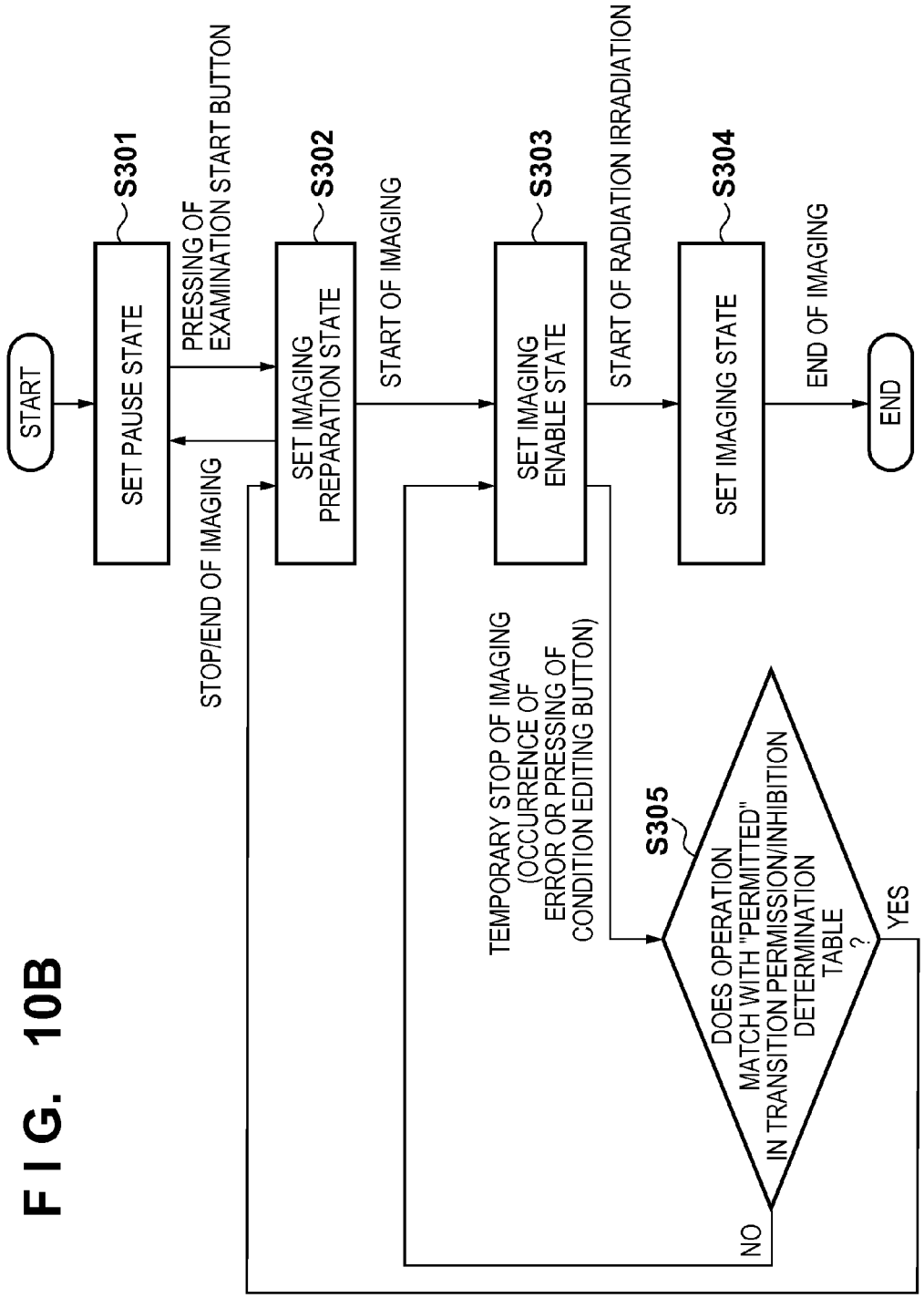
FIG. 10B is a flowchart showing a processing procedure according to the third embodiment.

A processing procedure according to this embodiment will be described below with reference to the flowchart of FIG. 10B. This embodiment will exemplify a case in which the radiation imaging apparatus 101 performs radiation imaging.

In step S301, the radiation imaging apparatus 101 is in the pause state. When starting imaging preparation, the process shifts to step S302. An external display apparatus 40 displays a condition editing screen (information input screen) 404 (FIG. 4A). When the radiation imaging apparatus 101 is set in the pause state, the state in step S301 is set. When the operator presses an examination start button 520 on the condition editing screen 404, the display screen transitions to a radiation imaging screen 401 (FIG. 4B). The process shifts to step S302.

In step S302, the radiation imaging apparatus 101 is in the imaging preparation state. When starting imaging operation, the process shifts to step S303. When stopping/finishing imaging operation, the process shifts to step S301.

In step S303, the radiation imaging apparatus 101 is in the imaging enable state. A display control unit 1022 causes the external display apparatus 40 to display the radiation imaging screen 401 (imaging enable screen) like that shown in FIG. 4B. When the radiation generating apparatus 20 starts radiation irradiation in response to the time when the operator presses the radiation irradiation switch, the process shifts to step S304. When temporarily stopping imaging operation, the process shifts to step S305.

In step S304, the radiation imaging apparatus 101 is in the imaging state. Upon completion of the imaging operation, the apparatus terminates the processing.

In step S305, in response to the operation of temporarily stopping the imaging operation, a console 102 controls a transition in accordance with the conditions of a transition permission/inhibition determination table like that shown in FIG. 11 (to be described later). If "permitted" is determined in the transition permission/inhibition determination table, the process shifts to step S302. If "inhibited" is determined, the process returns to step S303.

FIG. 11 shows a transition permission/inhibition determination table indicating permission/inhibition of a screen transition when the radiation imaging apparatus as an imaging target is in the imaging enable state in step S303 and the display control unit 1022 causes the external display apparatus 40 to display the radiation imaging screen 401 (FIG. 4B). The inhibition of a transition to another screen is controlled based on a transition permission/inhibition determination table determined in advance in accordance with the type of imaging mode of the radiation imaging apparatus and event detection contents obtained by an operation detection unit.

Referring to FIG. 11, the occurrence conditions for operation detected by an operation detection unit 1021 are classified into external causes and internal causes. An external cause is equivalent to the detection of operation by the operator via an external UI apparatus 30. An internal cause indicates that internal processing in the radiation imaging system is automatically detected. For example, an internal cause is equivalent to a start/end event that notifies the start/end of some kind of processing or an internal error event that notifies that an error has internally occurred.

In this embodiment, internal error events are classified into three types, namely "Warning" that indicates that imaging can be continued while giving a warning to the operator, "Error" that notifies that an error has internally occurred although it is possible to continue imaging, and "Fatal" that notifies the occurrence of an error that disables the continuation of imaging.

In addition, referring to FIG. 11, conditions also differ depending on the arrangement of the radiation imaging apparatus connected to the console 102. In this embodiment, the radiation imaging apparatuses are classified into three types, namely a type A imaging apparatus which operates only in the communication imaging mode, a type B imaging apparatus which operates only in the non-communication imaging mode, and a type C imaging apparatus which has the communication imaging mode and the non-communication imaging mode and can operate in either of the modes.

When only a type A imaging apparatus is connected to the console 102, a transition is "permitted" in all cases regardless of operation occurrence conditions. In this embodiment, since only the radiation imaging apparatus 101 which is a type A imaging apparatus is connected to the console 102, a transition is "permitted", and the process shifts to step S302.

When a type A imaging apparatus and a type B imaging apparatus are connected to the console 102, a transition is "permitted" in all cases regardless of operation occurrence conditions at the time of imaging by the type A imaging apparatus. At the time of imaging by the type B imaging apparatus, a transition is "permitted" only when an internal error belonging to "Fatal" occurs.

Assume that three or more imaging apparatuses are connected to the console 102. When the apparatuses are performing imaging in the communication imaging mode, a transition is "permitted" regardless of operation occurrence conditions. When the apparatuses are performing imaging in the non-communication imaging mode, a transition is "permitted" only when an internal error belonging to "Fatal" occurs.

Assume that when a radiation imaging apparatus of type B having only the non-communication imaging mode is singly connected to the console 102, a transition is "permitted" only when an error that disables the continuation of imaging occurs. When an error that enables the continuation of imaging has occurred, a transition is "inhibited", and the process returns to step S303.

Assume that the console 102 is connected to a radiation imaging apparatus of type C which has the communication imaging mode and the non-communication imaging mode and a radiation imaging apparatus of type A, and the radiation imaging apparatus of type C is in use. In this case, the permission/inhibition of a transition changes in accordance with the imaging mode in use. If the communication imaging mode is in use, a transition is "permitted" when an error that enables the continuation of imaging has occurred, and the process shifts to step S302. The radiation imaging apparatus 101 then enters the imaging preparation state. In contrast to this, if the non-communication mode is in use, a transition is "inhibited" when an error that enables the continuation of imaging has occurred, and the process returns to step S303.

Processing corresponding to the type of imaging mode and an error level will be described in more detail below. Upon detecting that the operator has performed the operation of temporarily stopping imaging, the operation detection unit 1021 notifies the display control unit 1022 of the operation content.

The display control unit 1022 performs determination processing in step S305. If, for example, the above operation is operation by the external UI apparatus 30, the display control unit 1022 determines that the operation corresponds to an operation occurrence condition belonging to "external cause" shown in FIG. 11. In addition, if a plurality of radiation imaging apparatuses are connected to the console 102, and a radiation imaging apparatus in the imaging enable state is operating in the communication imaging mode, "permitted" is determined, and the display control unit 1022 causes the external display apparatus 40 to display a screen corresponding to the operation. In addition, an imaging apparatus control unit 1023 causes the target radiation imaging apparatus to transition to the imaging preparation state as indicated in step S302.

In addition, if the above operation is error notification by internal processing, the display control unit 1022 determines an operation occurrence condition belonging to "internal cause" shown in FIG. 11. In addition, if the error level is that of "Warning" that enables the continuation of imaging and a radiation imaging apparatus in the imaging enable state is operating in the non-communication imaging mode, the display control unit 1022 determines "inhibited" and does not make any screen transition. Furthermore, the imaging apparatus control unit 1023 does not issue a state transition instruction to the target radiation imaging apparatus. The imaging enable state in step S303 remains.

In addition, if the above operation is an error notification by internal processing, the display control unit 1022 determines an operation occurrence condition belonging to "internal cause" shown in FIG. 11. Furthermore, if the error level is that of "Fatal" that disables the continuation of imaging, and a radiation imaging apparatus in the managing enable state is operating in the non-communication imaging mode, the display control unit 1022 determines "permitted" and causes the external display apparatus 40 to display a warning screen 4015 in FIG. 8B. The imaging apparatus control unit 1023 also causes the target radiation imaging apparatus to transition to the imaging preparation state in step S302.

Note that the content of the transition permission/inhibition determination table shown in FIG. 11 may have a different combination. If, for example, an error that requires to display a warning screen for the radiation imaging system has occurred although radiation imaging can be continued, the warning screen may be displayed.

In this embodiment, if a radiation imaging apparatus is in the imaging enable state and is displaying an imaging enable screen, the inhibition of a transition to another screen other than the examination end screen is controlled in accordance with conditions determined in the transition permission/inhibition determination table.

This makes it possible to suppress the occurrence of an unexpected screen transition by more precise control, when the operator actually performs imaging, in accordance with the imaging mode of the radiation imaging apparatus and operation occurrence conditions.

According to the present invention, it is possible to reduce the possibility of misshooting by suppressing the occurrence of a screen transition unexpected by the operator at the time of actual imaging while achieving power saving.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-044724 filed on Mar. 6, 2013, which is hereby incorporated by reference herein in its entirety.

What is claimed is:

1. A radiation imaging system comprising:
   a radiation imaging apparatus that captures a radiation image that is based on radiation irradiated from a radiation generation apparatus; and
   a control apparatus configured to control said radiation imaging apparatus,
   said control apparatus comprising a processor and memory, said processor and memory cooperating to
   control display of an imaging enable screen that enables said radiation imaging apparatus to perform imaging;
   detect at least an operation for finishing a radiation imaging examination and an operation other than an operation for finishing a radiation imaging examination; and
   determine a first imaging mode that performs radiation imaging in which a communication with said radiation generation apparatus is performed and an imaging timing is matched, and a second imaging mode that performs radiation imaging in which said radiation imaging apparatus itself detects radiation irradiated from said radiation generation apparatus and starts an accumulation operation of accumulating the radiation, wherein said radiation imaging system is switchable between said first and said second imaging modes, when said radiation imaging apparatus operates in the first imaging mode, a transition from the imaging enable screen to another screen other than the imaging enable screen is not inhibited, and when said radiation imaging apparatus operates in the second imaging mode, (i) in the case that an operation other than an operation for finishing a radiation imaging examination is detected while the imaging enable screen is displayed, a transition from the imaging enable screen to another screen related to the operation other than the operation for finishing a radiation imaging examination is inhibited and the control apparatus keeps the radiation imaging apparatus in an imaging enable state, and (ii) in the case that the operation for finishing a radiation imaging examination is detected while the imaging enable screen is displayed, a transition from the imaging enable screen to an examination end screen is implemented and the control apparatus changes the radiation imaging apparatus from the imaging enable state to an imaging preparation state.

2. The system according to claim 1, wherein the other screen includes at least one of:

a past image reference screen for reference to an image captured in the past by radiation imaging;

an error warning screen to be superimposed on the imaging enable screen when an error has occurred in the radiation imaging system;

a screen saver screen to be displayed when said processor accepts no operation for a certain time; and a condition editing screen for editing an imaging condition for the radiation imaging.

3. The system according to claim 1, wherein said processor further detects occurrence of an error in internal processing in said control apparatus, said processor and memory of said control apparatus further cooperate to determine whether the error is an error of a level that disables continuation of radiation imaging, and a transition from the imaging enable screen to the other screen is inhibited when said processor determines that the error is an error of a level that enables continuation of the radiation imaging.

4. The system according to claim 1, wherein said processor controls inhibition of a transition from the imaging enable screen to the other screen based on a transition permission/inhibition determination table determined in advance in accordance with types of imaging modes of said radiation imaging apparatus and detection contents detected by said processor.

5. The system according to claim 1, wherein in the imaging preparation state, a radiation detection unit of the radiation imaging apparatus is not energized and hence cannot detect the radiation emitted from the radiation generating apparatus.

6. The system according to claim 1, wherein in the imaging enable state, a radiation detection unit of the radiation imaging apparatus is energized and hence can detect the radiation emitted from the radiation generating apparatus.

7. The system according to claim 1, wherein the power consumption in the imaging enable state is higher than that in the imaging preparation state.

8. A control apparatus which controls operation of a radiation imaging apparatus that captures a radiation image that is based on radiation irradiated from a radiation generation apparatus, the control apparatus comprising:

a processor and memory, cooperating to function as a control unit configured to control display of an imaging enable screen that enables the radiation imaging apparatus to perform imaging;

an operation detection unit configured to detect at least an operation for finishing a radiation imaging examination and an operation other than an operation for finishing a radiation imaging examination;

an inhibition unit configured to inhibit a transition from the imaging enable screen to another screen other than the imaging enable screen; and a determination unit configured to determine a first imaging mode that performs radiation imaging in which a communication with the radiation generation apparatus is performed and an imaging timing is matched, and a second imaging mode that performs radiation imaging in which the radiation imaging apparatus itself detects radiation irradiated from the radiation generation apparatus and starts an accumulation operation of accumulating the radiation, wherein said imaging radiation system is switchable between said first and said second imaging modes, when the radiation imaging apparatus operates in the first imaging mode, said inhibition unit does not inhibit a transition from the imaging enable screen to another screen other than the imaging enable screen, and when the radiation imaging apparatus operates in the second imaging mode, (i) in the case that an operation other than an operation for finishing a radiation imaging examination is detected while the imaging enable screen is displayed, said inhibition unit inhibits a transition from the imaging enable screen to another screen related to the operation other than the operation for finishing a radiation imaging examination and the control apparatus keeps the radiation imaging apparatus in an imaging enable state, and (ii) in the case that the operation for finishing a radiation imaging examination is detected while the imaging enable screen is displayed, a transition from the imaging enable screen to an examination end screen is implemented and the control apparatus changes the radiation imaging apparatus from the imaging enable state to an imaging preparation.

9. A control method for a control apparatus which controls operation of a radiation imaging apparatus that captures a radiation image that is based on radiation irradiated from a radiation generation apparatus, the method comprising steps of:

controlling display of an imaging enable screen that enables the radiation imaging apparatus to perform imaging;

detecting at least an operation for finishing a radiation imaging examination and an operation other than an operation for finishing a radiation imaging examination; and determining a first imaging mode that performs radiation imaging while communicating with the radiation generation apparatus and while an imaging timing is matched, and a second imaging mode that performs radiation imaging in which the radiation imaging apparatus itself detects radiation irradiated from the radiation generation apparatus and starts an accumulation operation of accumulating the radiation, wherein said radiation imaging apparatus is switchable between said first and said second imaging modes, a transition from the imaging enable screen to another screen other than the imaging enable screen is not inhibited when the radiation imaging apparatus operates in the first imaging mode, and when the radiation imaging apparatus operates in the second imaging mode, (i) in the case that an operation other than an operation for finishing a radiation imaging examination is detected while the imaging enable screen is displayed, a transition from the imaging enable screen to another screen related to the operation other than the operation for finishing a radiation imagine examination is inhibited and the radiation imaging apparatus is kept in an imaging enable state, and (ii) in the case that the operation for finishing a radiation imaging examination is detected while the imaging enable screen is displayed, a transition from the imaging enable screen to an examination end screen is implemented and the radiation imaging apparatus is changed from the imaging enable state to an imaging preparation state.

10. A non-transitory computer-readable storage medium storing a computer program for causing a computer to execute each step in a control method for a control apparatus which controls operation of a radiation imaging apparatus that captures a radiation image that is based on radiation irradiated from a radiation generation apparatus, the method comprising steps of:

controlling display of an imaging enable screen that enables the radiation imaging apparatus to perform imaging;

detecting at least an operation for finishing a radiation imaging examination and an operation other than an operation for finishing a radiation imaging examination; and determining a first imaging mode that performs radiation imaging in which a communication with the radiation generation apparatus is performed and an imaging timing is matched, and a second imaging mode that performs radiation imaging in which the radiation imaging apparatus itself detects radiation irradiated from the radiation generation apparatus and starts an accumulation operation of accumulating the radiation, wherein said radiation imaging apparatus is switchable between said first and said second imaging modes, a transition from the imaging enable screen to another screen other than the imaging enable screen is not inhibited when the radiation imaging apparatus operates in the first imaging mode, and when the radiation imaging apparatus operates in the second imaging mode, (i) in the case that an operation other than an operation for finishing a radiation imaging examination is detected while the imaging enable screen is displayed, a transition from the imaging enable screen to another screen related to the operation other than the operation for finishing a radiation imaging examination is inhibited and the radiation imaging apparatus is kept in an imaging enable state, and (ii) in the case that the operation for finishing a radiation imaging examination is detected while the imaging enable screen is displayed, a transition from the imaging enable screen to an examination end screen is implemented and the radiation imaging apparatus is changed from the imaging enable state to an imaging preparation state.

11. A radiation imaging system comprising:

a radiation imaging apparatus that captures a radiation image that is based on radiation irradiated from a radiation generation apparatus; and a control apparatus configured to control the radiation imaging apparatus, the control apparatus comprising a processor and memory, the processor and memory cooperating to control display of an imaging enable screen that enables the radiation imaging apparatus to perform imaging, detect at least an operation for finishing a radiation imaging examination and an operation other than an operation for finishing a radiation imaging examination, and determine an imaging mode that performs radiation imaging in which the radiation imaging apparatus itself detects radiation irradiated from the radiation generation apparatus and starts an accumulation operation of accumulating the radiation, wherein when the radiation imaging apparatus operates in the imaging mode, (i) in the case that an operation other than an operation for finishing a radiation imaging examination is detected while the imaging enable screen is displayed, a transition from the imaging enable screen to another screen related to the operation other than the operation for finishing a radiation imaging examination is inhibited and the control apparatus keeps the radiation imaging apparatus in an imaging enable state, and (ii) in the case that the operation for finishing a radiation imaging examination is detected while the imaging enable screen is displayed, a transition from the imaging enable screen to an examination end screen is implemented and the control apparatus changes the radiation imaging apparatus from the imaging enable state to an imaging preparation state.

12. The system according to claim 11, wherein in the imaging preparation state, a radiation detection unit of the radiation imaging apparatus is not energized and hence cannot detect the radiation emitted from the radiation generating apparatus.

13. The system according to claim 11, wherein in the imaging enable state, a radiation detection unit of the radiation imaging apparatus is energized and hence can detect the radiation emitted from the radiation generating apparatus.

14. The system according to claim 11, wherein the power consumption in the imaging enable state is higher than that in the imaging preparation state.

15. A control apparatus which controls operation of a radiation imaging apparatus that captures a radiation image that is based on radiation irradiated from a radiation generation apparatus, the control apparatus comprising a processor and memory, cooperating to:

control display of an imaging enable screen that enables the radiation imaging apparatus to perform imaging;

detect at least an operation for finishing a radiation imaging examination and an operation other than an operation for finishing a radiation imaging examination;

inhibit a transition from the imaging enable screen to another screen other than the imaging enable screen; and determine an imaging mode that performs radiation imaging in which the radiation imaging apparatus itself detects radiation irradiated from the radiation generation apparatus and starts an accumulation operation of accumulating the radiation, wherein when the radiation imaging apparatus operates in the imaging mode, in the case that an operation other than an operation for finishing a radiation imaging examination is detected while the imaging enable screen is displayed, a transition from the imaging enable screen to another screen related to the operation other than the operation for finishing a radiation imaging examination is inhibited and the control apparatus keeps the radiation imaging apparatus in an imaging enable state, and in the case that the operation for finishing a radiation imaging examination is detected while the imaging enable screen is displayed, a transition from the imaging enable screen to the operation for finishing a radiation imaging examination and the control apparatus changes the radiation imaging apparatus from the imaging enable state to an imaging preparation state.

16. A control method for a control apparatus which controls operation of a radiation imaging apparatus that captures a radiation image that is based on radiation irradiated from a radiation generation apparatus, the method comprising steps of:

controlling display of an imaging enable screen that enables the radiation imaging apparatus to perform imaging;

detecting at least an operation for finishing a radiation imaging examination and an operation other than an operation for finishing a radiation imaging examination; and determining an imaging mode that performs radiation imaging in which the radiation imaging apparatus itself detects radiation irradiated from the radiation generation apparatus and starts an accumulation operation of accumulating the radiation, wherein when the radiation imaging apparatus operates in the imaging mode, in the case that an operation other than an operation for finishing a radiation imaging examination is detected while the imaging enable screen is displayed, a transition from the imaging enable screen to another screen related to the operation other than the operation for finishing a radiation imaging examination is inhibited and the radiation imaging apparatus is kept in an imaging enable state, and in the case that the operation for finishing a radiation imaging examination is detected while the imaging enable screen is displayed, a transition from the imaging enable screen to an examination end screen is implemented and the radiation imaging apparatus is changed from the imaging enable state to an imaging preparation state.

17. A non-transitory computer-readable storage medium storing a computer program for causing a computer to execute each step in a control method for a control apparatus which controls operation of a radiation imaging apparatus that captures a radiation image that is based on radiation irradiated from a radiation generation apparatus, the method comprising steps of:

controlling display of an imaging enable screen that enables the radiation imaging apparatus to perform imaging;

detecting at least an operation for finishing a radiation imaging examination and an operation other than an operation for finishing a radiation imaging examination; and determining an imaging mode that performs radiation imaging in which the radiation imaging apparatus itself detects radiation irradiated from the radiation generation apparatus and starts an accumulation operation of accumulating the radiation, wherein when the radiation imaging apparatus operates in the imaging mode, in the case that an operation other than an operation for finishing a radiation imaging examination is detected while the imaging enable screen is displayed, a transition from the imaging enable screen to another screen related to the operation other than the operation for finishing a radiation imaging examination is inhibited and the radiation imaging apparatus is kept in an imaging enable state, and in the case that the operation for finishing a radiation imaging examination is detected while the imaging enable screen is displayed, a transition from the imaging enable screen to an examination end screen is implemented and the radiation imaging apparatus is changed from the imaging enable state to an imaging preparation state.

* * * * *